(12) United States Patent
Brenner et al.

(10) Patent No.: US 11,071,747 B2
(45) Date of Patent: Jul. 27, 2021

(54) USE OF NAD PRECURSORS FOR BREAST ENHANCEMENT

(71) Applicant: UNIVERSITY OF IOWA RESEARCH FOUNDATION, Iowa City, IA (US)

(72) Inventors: Charles M. Brenner, Iowa City, IA (US); Po Hien Ear, Iowa City, IA (US); Ankita Chadda, Iowa City, IA (US); Amy Sindler, Iowa City, IA (US); Marie E. Migaud, Lurgan (GB)

(73) Assignee: UNIVERSITY OF IOWA RESEARCH FOUNDATION, Iowa City, IA (US)

( * ) Notice: Subject to any disclaimer, the term of this patent is extended or adjusted under 35 U.S.C. 154(b) by 0 days.

(21) Appl. No.: 15/826,073

(22) Filed: Nov. 29, 2017

(65) Prior Publication Data

US 2018/0147225 A1    May 31, 2018

Related U.S. Application Data

(60) Provisional application No. 62/427,666, filed on Nov. 29, 2016.

(51) Int. Cl.
*A01N 43/04* (2006.01)
*A61K 31/70* (2006.01)
*A61K 31/706* (2006.01)

(52) U.S. Cl.
CPC .................................. *A61K 31/706* (2013.01)

(58) Field of Classification Search
None
See application file for complete search history.

(56) References Cited

U.S. PATENT DOCUMENTS

| | | | |
|---|---|---|---|
| 4,559,157 A | 12/1985 | Smith et al. |
| 4,608,392 A | 8/1986 | Jacquet et al. |
| 4,820,508 A | 4/1989 | Wortzman |
| 4,938,949 A | 7/1990 | Borch et al. |
| 4,992,478 A | 2/1991 | Geria |
| 5,055,460 A | 10/1991 | Friedlander |
| 6,255,291 B1 | 7/2001 | Germano |
| 6,624,150 B2 | 9/2003 | Yerxa et al. |
| 6,867,231 B1 | 3/2005 | Burke et al. |
| 7,022,680 B2 | 4/2006 | Sauve et al. |
| 7,138,122 B2 | 11/2006 | Burke et al. |
| 7,179,791 B2 | 2/2007 | Stamler et al. |
| 7,544,497 B2 | 6/2009 | Sinclair et al. |
| 7,601,332 B2 | 10/2009 | Vlahov et al. |
| 7,615,535 B2 | 11/2009 | Stamler et al. |
| 7,776,326 B2 | 8/2010 | Milbrandt et al. |
| 7,977,049 B2 | 7/2011 | Sinclair et al. |
| 8,105,568 B2 | 1/2012 | Vlahov et al. |
| 8,106,184 B2 | 1/2012 | Sauve et al. |
| 8,114,626 B2 | 2/2012 | Brenner et al. |
| 8,197,807 B2 | 6/2012 | Brenner |
| 8,217,006 B2 | 7/2012 | Stamler et al. |
| 8,383,086 B2 | 2/2013 | Brenner |
| 9,000,147 B2 | 4/2015 | Sauve et al. |
| 9,321,797 B2 | 4/2016 | Sauve et al. |
| 9,408,834 B2 | 8/2016 | Zemel et al. |
| 2002/0128205 A1 | 9/2002 | Stamler et al. |
| 2004/0224918 A1 | 11/2004 | Yatvin et al. |
| 2005/0227327 A1 | 10/2005 | Brenner |
| 2006/0025337 A1 | 2/2006 | Sinclair et al. |
| 2006/0111435 A1 | 5/2006 | Sinclair et al. |
| 2006/0229265 A1* | 10/2006 | Milburn ............ A61K 31/4436 514/43 |
| 2007/0117765 A1 | 5/2007 | Sauve et al. |
| 2008/0194803 A1 | 8/2008 | Sinclair et al. |
| 2008/0318892 A1 | 12/2008 | Pickering et al. |
| 2009/0069444 A1 | 3/2009 | Joseph et al. |
| 2009/0196942 A1 | 8/2009 | Goyarts et al. |
| 2009/0270503 A1 | 10/2009 | Hermelin et al. |
| 2012/0108535 A1 | 5/2012 | Sauve et al. |
| 2012/0172584 A1 | 7/2012 | Sauve et al. |
| 2012/0251463 A1 | 10/2012 | Brenner |
| 2012/0328526 A1 | 12/2012 | Kristian |
| 2012/0329748 A1 | 12/2012 | Sauve et al. |
| 2013/0011377 A1 | 1/2013 | Perrin et al. |
| 2013/0165398 A1 | 6/2013 | Huber |
| 2014/0113928 A1 | 4/2014 | Albaghdadi et al. |
| 2015/0056274 A1 | 2/2015 | Zemel et al. |
| 2015/0175645 A1 | 6/2015 | Milburn et al. |
| 2016/0000745 A1 | 1/2016 | Gojon-Zorrilla et al. |
| 2016/0250241 A1 | 9/2016 | Deren-Lewis et al. |

(Continued)

FOREIGN PATENT DOCUMENTS

| CH | 318073 A | 12/1956 |
|---|---|---|
| EP | 2805719 A1 | 11/2014 |

(Continued)

OTHER PUBLICATIONS

Yuvaraj et al. Breast Cancer Res. Treat (2009), vol. 114, pp. 377-384.*
Yoon et al. Cell Metabolism (2015), vol. 21, pp. 706-717.*
Thiry, J , et al., "A review of pharmaceutical extrusion: Critical process parameters and scaling-up", International Journal of Pharmaceutics 479, 227-240 (2015).
Thong, H , et al., "Percutaneous penetration enhancers: an overview", Skin Pharmacol Physiol 20(6), 272-282 (2007).
Trammell, S , et al., "Nicotinamide Riboside Is a Major NAD+ Precursor Vitamin in Cow Milk 1-3", Journal of Nutrition 146(5), 957-963 (2016).

(Continued)

*Primary Examiner* — Patrick T Lewis
(74) *Attorney, Agent, or Firm* — Viksnins Harris Padys Malen LLP

(57) ABSTRACT

Certain embodiments of the invention provide a method for breast enhancement in a female mammal (e.g., a human) in need thereof, comprising administering an effective amount of a nicotinamide adenine dinucleotide (NAD) precursor to the mammal.

14 Claims, 8 Drawing Sheets

(56) References Cited

U.S. PATENT DOCUMENTS

| | | | |
|---|---|---|---|
| 2016/0272668 | A1 | 9/2016 | Dellinger et al. |
| 2016/0355539 | A1 | 12/2016 | Migaud et al. |
| 2017/0267709 | A1 | 9/2017 | Migaud et al. |
| 2017/0304338 | A1 | 10/2017 | Dellinger et al. |

FOREIGN PATENT DOCUMENTS

| | | | |
|---|---|---|---|
| GB | 2542881 | A | 4/2017 |
| KR | 101604212 | B1 | 3/2016 |
| WO | 2003093290 | A2 | 11/2003 |
| WO | 2006116322 | A2 | 11/2006 |
| WO | 2013002880 | A1 | 1/2013 |
| WO | 2013045538 | A1 | 4/2013 |
| WO | 2014011676 | A1 | 1/2014 |
| WO | 2014014828 | A1 | 1/2014 |
| WO | 2014059031 | A2 | 4/2014 |
| WO | 2015014722 | A1 | 2/2015 |
| WO | 2015016829 | A1 | 2/2015 |
| WO | 2015066382 | A1 | 5/2015 |
| WO | 2015186068 | A1 | 12/2015 |
| WO | 2015186114 | A1 | 12/2015 |
| WO | 2016014927 | A2 | 1/2016 |
| WO | 2016049236 | A1 | 3/2016 |
| WO | 2016111992 | A1 | 7/2016 |
| WO | 2016144660 | A1 | 9/2016 |
| WO | 2016149277 | A1 | 9/2016 |
| WO | 2018102426 | A1 | 6/2018 |

OTHER PUBLICATIONS

Trammell, S., "Nicotinamide riboside is uniquely and orally bioavailable in mice and humans", Nature Comm 7, 12948, 14 pages (2016).
Trammell, S., "Nicotinamide Riboside Opposes Type 2 Diabetes and Neuropathy in Mice", Scientific Reports 6, 2693, 7 pages (2016).
Trask, A., et al., "Achieving Polymorphic and Stoichiometric Diversity in Cocrystal Formation: Importance of Solid-State Grinding, Powder X-ray Structure Determination, and Seeding", Crystal Growth & Design 5(6), 2233-2241 (2005).
Trask, A, et al., "Screening for crystalline salts via mechanochemistry", Chem Commun 51-53 (2006).
Urberg, M., et al., "Evidence for Synergism Between Chromium and Nicotinic Acid in the Control of Glucose Tolerance in Elderly Humans", Metabolism 36(9), 896-899 (1987).
Verhoeven, E, et al., "Influence of formulation and process parameters on the release characteristics of ethylcellulose sustained-release mini-matrices produced by hot-melt extrusion", European Journal of Pharmaceutics and Biopharmaceutics 69, 312-319 (2008).
Verhoeven, E, et al., "Xanthan gum to tailor drug release of sustained-release ethylcellulose mini-matrices prepared via hot-melt extrusion: in vitro and in vivo evaluation", European Journal of Pharmaceutics and Biopharmaceutics 63, 320-330 (2006).
Wahl, P, et al., "Inline monitoring and a PAT strategy for pharmaceutical hotmelt extrusion", International Journal of Pharmaceutics 455, 159-168 (2013).
Xu, P, et al., "Vitamin B3, the nicotinamide adenine dinucleotides and aging", Mechanisms of Ageing and Development 131, 287-298 (2010).
Yoshikawa, M, et al., "Studies of Phosphorylation. III. Selective Phosphorylation of Unprotected Nucleosides", Bulletin of the Chemical Society of Japan 42, 3505-3508 (1969).
Almeida, A, et al., "Upscaling and in-line process monitoring via spectroscopic techniques of ethylene vinyl acetate hot-melt extruded formulations", International Journal of Pharmaceutics 439, 223-229 (2012).
Ansel, "Section IV Semisolid Dosage Forms and Transdermal Systems", Pharmaceutical Dosage Forms Drug Delivery Systems 9th Ed, Chapter 10, 22 pages (2011).
Applegate, L, et al., "Identification of the Molecular Target for the Suppression of Contact Hypersensitivity", J Exp Med 170, 1117-1131 (1989).

Baker, H, et al., "Vitamin profile of 563 gravidas during trimesters of pregnancy", J Am Coll Nutr 21(1), 33-37 (2002).
Berge, S., et al., "Pharmaceutical Salts", Journal of Pharmaceutical Sciences, vol. 66, No. 1, 1-19 (1977).
Bieganowski, P, et al., "Discoveries of Nicotinamide Riboside as a Nutrient and Conserved NRK Genes Establish a Preiss-Handler Independent Route to NAD+ in Fungi and Humans", Cell 117(4), 495-502 (2004).
Biospace, "ChromaDex, Inc. Initiates First Human Clinical Study to Confirm ChromaDex's NIAGEN TM Nicotinamide Riboside Will Increase NAD+", http://www.biospace.com/News/chromadex-inc-initiates-first-human-clinical-study/339980, 6 pages (2014).
Breitenbach, J, "Melt extrusion: from process to drug delivery technology", European Journal of Pharmaceutics and Biopharmaceutics 54, 107-117 (2002).
Bruce, L, et al., "Properties of hot-melt extruded tablet formulations for the colonic delivery of 5-aminosalicylic acid", European Journal of Pharmaceutics and Biopharmaceutics 59, 85-97 (2005).
Bzowska, A, et al., "Purine nucleoside phosphorylases: properties, functions, and clinical aspects", Pharmacology & Therapeutics 88, 249-425 (2000).
Canto, C, et al., "Crosstalk between poly(ADP-ribose) polymerase and sirtuin enzymes", Molecular Aspects of Medicine 34, 1168-1201 (2013).
Conze, D, et al., "Safety assessment of nicotinamide riboside, a form of vitamin B3", Hum Exp Toxicol 35(11), 1149-1160 (2016).
Crossey, K, et al., "Exploiting the use of ionic liquids to access phosphorodiamidites", RSC Advances 2, 2988-2993 (2012).
Crossey, K, et al., "Nucleoside phosphitylation using ionic liquid stabilised phosphorodiamidites and mechanochemistry", Chem Commun 48, 11969-11971 (2012).
Crowley, M, et al., "Pharmaceutical Applications of Hot-Melt Extrusion: Part I", Drug Development and Industrial Pharmacy 33, 909-926 (2007).
Friedlos, F, et al., "Metabolism of nad(p)h by blood components: Relevance to bioreductively activated prodrugs in a targeted enzyme therapy system", Biochem Pharmacol 44(4), 631-635 (1992).
Gong, B, et al., "Nicotinamide riboside restores cognition through an upregulation of proliferator-activated receptor-g coactivator 1a regulated b-secretase 1 degradation and mitochondrial gene expression in Alzheimer's mouse models", Neurobiology of Aging 34, 1581-1588 (2013).
Haratake, A, et al., "UVB-Induced Alterations in Permeability Barrier Function: Roles for Epidermal Hyperproliferation and Thymocyte-Mediated Response", J Invest Dermatol 108, 769-775 (1997).
Hardacre, C, et al., "Overcoming hydrolytic sensitivity and low solubility of phosphitylation reagents by combining ionic liquids with mechanochemistry", Chem Commun 47, 5846-5848 (2011).
Hasa, D, et al., "Cocrystal Formation through Mechanochemistry: from Neat and Liquid-Assisted Grinding to Polymer-Assisted Grinding", Angew Chem Int Ed 54, 7371-7375 (2015).
Haynes, H, et al., "Codehydrogenases. Part II. A Synthesis of Nicotinamide Nucleotide", J Med Chem Soc, 3727-3732 (1957).
Hughey, J, et al., "The use of inorganic salts to improve the dissolution characteristics of tablets containing Soluplus®-based solid dispersions", European Journal of Pharmaceutical Sciences 48, 758-766 (2013).
Janssens, S, et al., "The use of a new hydrophilic polymer, Kollicoat IR®, in the formulation of solid dispersions of Itraconazole", European Journal of Pharmaceutical Sciences 30, 288-294 (2007).
Jarman, M, et al., "4-Substituted nicotinic acids and nicotinamides. Part III. Preparation of 4-methylnicotinic acid riboside", J Chem Soc (C), 918-920 (1969).
Jiang, S, et al., "Ultraviolet B-induced alterations of the skin barrier and epidermal calcium gradient", Exp Dermatol 16(12), 985-992 (2007).
Kahn, N, et al., "Effective treatment of mitochondrial myopathy by nicotinamide riboside, a vitamin B3", EMBO Mol Med 6(6), 721-731 (2014).
Karki, S, et al., "Screening for Pharmaceutical Cocrystal Hydrates via Neat and Liquid-Assisted Grinding", Molecular Pharmaceutics 4(3), 347-354 (2007).

(56) References Cited

OTHER PUBLICATIONS

Krier, F., et al., "PAT tools for the control of co-extrusion implants manufacturingprocess", International Journal of Pharmaceutics 458, 15-24 (2013).

Kulikova, V., et al., "Generation, Release, and Uptake of the NAD Precursor Nicotinic Acid Riboside by Human Cells", Journal of Biological Chemistry 290(45), 27124-27137 (2015).

Lee, J., et al., "A chemical synthesis of nicotinamide adenine dinucleotide (NAD+)", Chem Commun 729-730 (1999).

Liu, H., et al., "Effects of Screw Configuration on Indomethacin Dissolution Behavior in Eudragit E PO", Advances in Polymer Technology 31(4), 331-342 (2012).

Maniruzzaman, M., et al., "A Review of Hot-Melt Extrusion: Process Technology to Pharmaceutical Products", International Scholarly Research Network Pharmaceutics, Article ID 436763, 9 pages (2012).

Mikhailopulo, I., "Synthesis of Glycosides of Nicotinamide and Nicotinamide Mononucleotide", Synthesis 388-389 (1981).

Miller, D., et al., "Targeted Intestinal Delivery of Supersaturated Itraconazole for Improved Oral Absorption", Pharm Res 25, 1450, 32 pages (2008).

Nakamichi, K., et al., "The role of the kneading paddle and the effects of screw revolution speed and water content on the preparation of solid dispersions using a twin-screw extruder", International Journal of Pharmaceutics 241, 203-211 (2002).

Oba, C., et al., "Collagen hydrolysate intake improves the loss of epidermal barrier function and skin elasticity induced by UVB irradiation in hairless mice", Photodermatol Photoimmunol Photomed 29(4), 204-211 (2013).

Pankiewicz, K., "Novel Nicotinamide Adenine Dinucleotide Analogues as Potential Anticancer Agents: Quest for Specific Inhibition of Inosine Monophosphate Dehydrogenase", Pharmacol Ther 76, 1-3, 89-100 (1997).

Paudel, K., et al., "Challenges and opportunities in dermal/transdermal delivery", Ther Deliv 1(1), 109-131 (2010).

Plasman, V., "Triterpene Saponins, Quaternary Ammonium Compounds, Phosphatidyl Cholines, and Amino Acids in the Pronotal and Elytral Secretions of Platyphora opima and Desmogramma subtropica", J Nat Prod 63, 1261-1264 (2000).

Ravalico, F., et al., "Rapid synthesis of nucleotide pyrophosphate linkages in a ball mill", Organic & Biomolecular Chemistry 9, 6496-6497 (2011).

Redpath, P., et al., "INettiercotinamide Benzimidazolide Dinucleotides, Non-Cyclisable Analogues of NAD+", Synlett 25, 2331-2336 (2014).

Reitz, E., et al., "Residence time modeling of hot melt extrusion processes", European Journal of Pharmaceutics and Biopharmaceutics 85, 1200-1205 (2013).

Repka, M., et al., "Pharmaceutical Applications of Hot-Melt Extrusion: Part II", Drug Development and Industrial Pharmacy 33, 1043-1057 (2007).

Romanski, F., et al., "The Importance of Monitoring Process Parameters as a Method for Quality Control for Hot Melt Extrusion", BASF Corp, 1 page (2013).

Sarode, A., et al., "Hot melt extrusion (HME) for amorphous solid dispersions: Predictive tools for processing and impact of drug-polymer interactions on supersaturation", European Journal of Pharmaceutical Sciences 48, 371-384 (2013).

Shah, S., et al., "Melt extrusion with poorly soluble drugs", International Journal of Pharmaceutics 453, 233-252 (2013).

Shan, N., et al., "Mechanochemistry and co-crystal formation: effect of solvent on reaction kinetics", Chem Commun, 2372-2373 (2002).

Surjana, D., et al., "Role of Nicotinamide in DNA Damage, Mutagenesis, and DNA Repair", Journal of Nucleic Acids, doi:10.4061/2010/157591, 13 pages (2010).

Tanimori, S., et al., "An Efficient Chemical Synthesis of Nicotinamide Riboside (NAR) and Analogues", Bioorganic & Medicinal Chemistry Letters 12, 1135-1137 (2002).

* cited by examiner

USE OF NAD PRECURSORS FOR BREAST ENHANCEMENT

RELATED APPLICATION

This application claims the benefit of priority of U.S. Provisional Application Ser. No. 62/427,666 filed on Nov. 29, 2016, which application is incorporated by reference herein.

BACKGROUND OF THE INVENTION

Female breast enhancement is a multibillion-dollar industry and includes both invasive and non-invasive methods. Invasive techniques include surgical implants and microsurgery (e.g., fat grafting). While the American Society for Aesthetic Plastic Surgery reported 271,292 cases of breast augmentation in 2014, there are a number of drawbacks to these procedures. For example, the procedures are costly, carry surgical risks, result in pain and discomfort, require follow-on maintenance procedures, are associated with long-term health risks from implant degradation, require narcotic and painkillers, may cause psychological trauma from having synthetic material in the body, and may limit movement and activity for extended periods. Because of these drawbacks, many women are choosing alternatives to surgery and microsurgery, by using herb-blends, pills, creams and external devices (e.g. suction cups). However, these alternatives also have their own disadvantages. Regarding the herbs/creams, there is generally is a lack of evidence for efficacy, long-term safety concerns and these products may result in untraceable effects the body's natural hormone levels. Thus, there is a need for new methods and therapies for breast enhancement and/or promoting mammary gland development.

SUMMARY OF THE INVENTION

Accordingly, certain embodiments of the invention provide a method for breast enhancement in a female mammal (e.g., a human) in need thereof, comprising administering an effective amount of a nicotinamide adenine dinucleotide (NAD) precursor to the mammal.

Certain embodiments of the invention provide a method for increasing mammary gland mass and/or volume in a female mammal (e.g., a human) in need thereof, comprising administering an effective amount of a nicotinamide adenine dinucleotide (NAD) precursor to the mammal.

Certain embodiments of the invention provide a method for promoting mammary gland development in a female mammal (e.g., a human) in need thereof, comprising administering an effective amount of a nicotinamide adenine dinucleotide (NAD) precursor to the mammal.

Certain embodiments of the invention provide a NAD precursor for breast enhancement in a female mammal (e.g., a human) in need thereof.

Certain embodiments of the invention provide the use of a NAD precursor to prepare a medicament for breast enhancement in a female mammal (e.g., a human) in need thereof.

Certain embodiments of the invention provide a NAD precursor for increasing mammary gland mass and/or volume in a female mammal (e.g., a human) in need thereof.

Certain embodiments of the invention provide the use of a NAD precursor to prepare a medicament for increasing mammary gland mass and/or volume in a female mammal (e.g., a human) in need thereof.

Certain embodiments of the invention provide a NAD precursor for promoting mammary gland development in a female mammal (e.g., a human) in need thereof.

Certain embodiments of the invention provide the use of a NAD precursor to prepare a medicament for promoting mammary gland development in a female mammal (e.g., a human) in need thereof.

Certain embodiments of the invention provide a composition (e.g., a pharmaceutical composition) for use in breast enhancement, increasing mammary gland mass and/or volume, and/or in promoting mammary gland development in a female mammal (e.g., a human) in need thereof, comprising a NAD precursor, and a pharmaceutically acceptable carrier (e.g., a pharmaceutically acceptable carrier).

Certain embodiments of the invention provide a kit comprising 1) a NAD precursor; and 2) instructions for administering the NAD precursor to a female mammal for breast enhancement, increasing mammary gland mass and/or volume, and/or in promoting mammary gland development in the female mammal.

Certain embodiments of the invention provide a kit comprising:

1) a composition (e.g., a pharmaceutical composition) comprising a NAD precursor and a carrier (e.g., a pharmaceutically acceptable carrier), wherein the composition is formulated for oral or topical administration; and 2) instructions for orally or topically administering the NAD precursor to a female mammal for breast enhancement, increasing mammary gland mass and/or volume, and/or promoting mammary gland development.

BRIEF DESCRIPTION OF THE FIGURES

FIG. 1A. NR-supplemented mothers have more massive mammary glands. FIG. 1B. Mammary glands 4 and 5 isolated from lactating females were stained with Carmine/Alum staining. NR-fed females have more lactating mammary tissue.

FIG. 2A. Twelve week-old female mice with NR supplementation for two weeks have more mammary gland with beige fat. FIG. 2B. Carmine/Alum staining of mammary glands. FIG. 2C. Quantification of mammary gland ductal length can be assessed by taking the measurement of the left (L1), right (L2), top (L3) and bottom (L4) branchings expressed in cm. FIG. 2D. NR supplementation increases the surface area of mammary gland #4-5. FIG. 2E. NR supplementation increases ductal length measurements as described in FIG. 2C.

FIG. 3A. Mammary gland #4-5 were isolated and the weight was recorded. NR-fed female rats have more mammary gland tissue. FIG. 3B. Images of dissected mammary gland #4-5. FIG. 3C. Weight of brown adipose tissue (BAT).

Figure 5A:
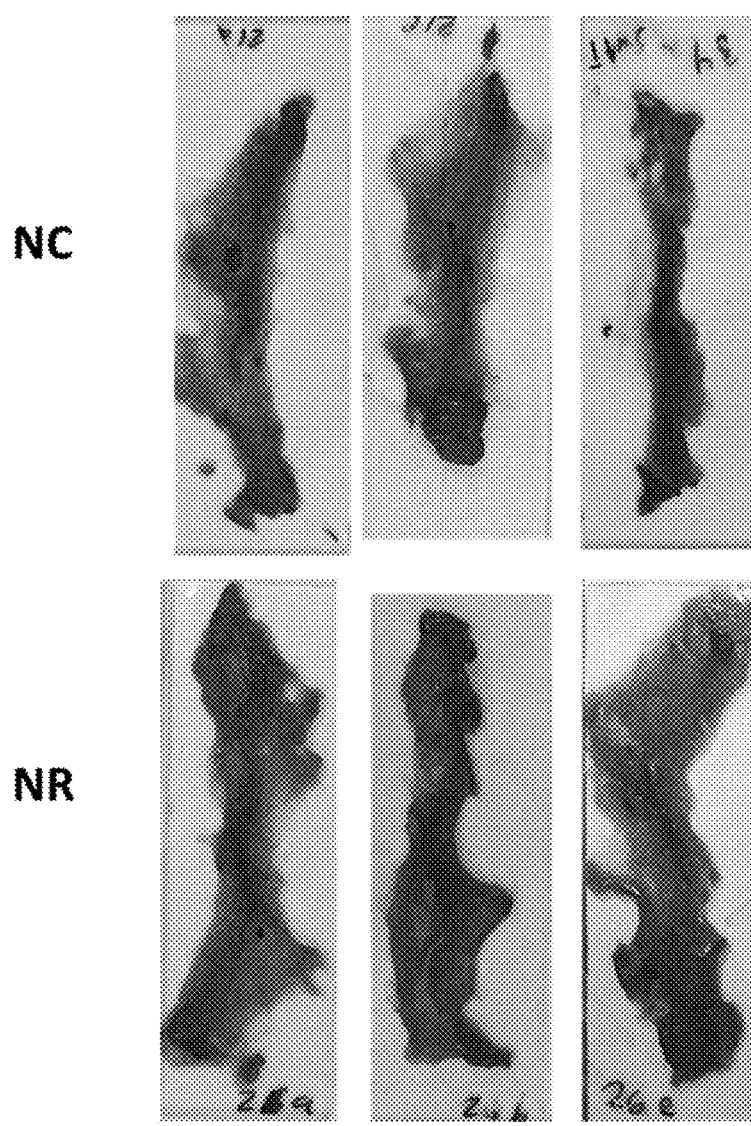
Figure 5B:
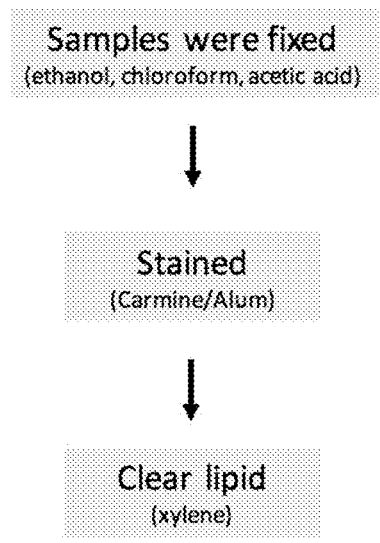
Figure 5B:
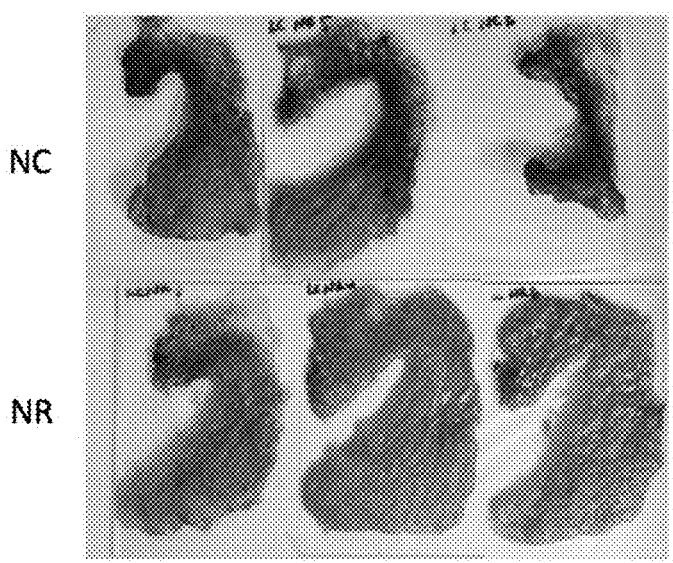

FIGS. 5A-B. NR-supplemented mammary tissue is partially resistant to xylene extraction. FIG. 5A. NR supplementation changes the fat composition of the mammary gland of female mice. Eight month-old female mice were on NC or NR diet for six weeks. Mammary glands #4-5 were isolated, fixed, stained with Carmine/Alum stain and xylene was use to extract fat. After 1 week of incubation in xylene, mammary glands from NR-fed mice have more fat remaining. FIG. 5B. NR-fed rats have mammary gland with a different fat composition. NR-fed rats develop mammary adipose tissue that is poorly cleared by xylene.

DETAILED DESCRIPTION

The invention described herein addresses the physical, emotional and/or medical challenges currently facing women seeking breast beautification and/or enlargement. Specifically, described herein is the use of a nicotinamide adenine dinucleotide (NAD) precursor, such as nicotinamide riboside (NR) or derivatives thereof, for breast enhancement in a female mammal. NR is a natural product, is currently produced under GMP, has achieved FDA new dietary ingredient status, and is generally regarded as safe (Bieganowski & Brenner, Cell (2004), 117(4), 495-502; Trammell, et al., Journal of Nutrition (2016), 146(5), 957-963). As such, NR may be used as an alternative to the current state of the art approaches to breast augmentation to safely and effectively enhance the female breast in a non-invasive, non-hormonal manner. For example, a NAD precursor may be administered to young women and women of reproductive age wishing to enhance their appearance; women of more advanced age seeking to slow the effect of aging on the firmness, shape and size of their breasts; and women who recently lactated.

METHODS OF THE INVENTION

Accordingly, certain embodiments of the invention provide a method for breast enhancement in a female mammal (e.g., a human) in need thereof, comprising administering an effective amount of a nicotinamide adenine dinucleotide (NAD) precursor to the mammal.

As used herein, the term "a mammal in need thereof" refers to any mammal wanting/desiring to practice a method described herein for any purpose.

As used herein, the term "breast enhancement" means increasing the firmness, improving the shape and/or increasing the size of a female breast (e.g., as compared to a control, such as to the firmness or size of the breast prior to administration). The term "size" may refer to mass or volume of the breast (e.g., bra cup size may increase). In certain embodiments, the breast firmness or size is increased by at least about 1%, 2%, 3%, 4%, 5%, 6%, 7%, 8%, 9% 10% or more. As used herein, the term "improved shape" includes both subjective and objective improvements to the shape of the breast.

As used herein, the term "in need thereof" refers to a female mammal that wishes to practice a method of the invention (e.g., breast enhancement, increasing mammary gland mass and/or volume, and/or promoting mammary gland development) for any purpose, e.g., for medical reasons, cosmetic reasons, etc.

Certain embodiments of the invention provide a method for increasing mammary gland mass and/or volume in a female mammal (e.g., a human) in need thereof, comprising administering an effective amount of a nicotinamide adenine dinucleotide (NAD) precursor to the mammal. Methods for measuring mammary gland mass/volume are known in the art, for example, using assays described in the Examples.

Certain embodiments of the invention provide a method for promoting mammary gland development in a female mammal (e.g., a human) in need thereof, comprising administering an effective amount of a nicotinamide adenine dinucleotide (NAD) precursor to the mammal.

As used herein, the term "mammary gland development" refers to the growth of mammary gland tissues, including, e.g., fat pad formation, epithelial branching, alveolar development and lobule development. Methods for evaluating mammary gland development are known in the art, for example, using assays described in the Examples.

In certain embodiments, administration of the NAD precursor increases the mammary gland mass and/or volume (e.g., as compared to a control, such as to the mass/volume of the mammary gland prior to administration). In certain embodiments, the mammary gland mass and/or volume is increased by at least about 1%, 2%, 3%, 4%, 5%, 6%, 7%, 8%, 9%, 10% or more.

In certain embodiments, administration of the NAD precursor increases fat pad formation, epithelial branching, alveolar development and/or lobule development (e.g., as compared to a control, such as to fat pad formation, epithelial branching, alveolar development and/or lobule development prior to administration). In certain embodiments, fat pad formation, epithelial branching, alveolar development and/or lobule development is increased by at least about 1%, 2%, 3%, 4%, 5%, 6%, 7%, 8%, 9%, 10% or more. Methods for measuring fat pad formation, epithelial branching, alveolar development and/or lobule development are known in the art, for example, using assays described in the Examples.

In certain embodiments, administration of the NAD precursor increases the adipose mass of the mammary gland (e.g., as compared to a control, such as to adipose mass of the mammary gland prior to administration). In certain embodiments, the adipose mass is increased by at least about 1%, 2%, 3%, 4%, 5%, 6%, 7%, 8%, 9%, 10% or more. In certain embodiments, the mass of the subcutaneous white adipose tissue (sWAT) is increased. In certain embodiments, the mass of the brown adipose tissue (BAT) is increased.

In certain embodiments, the NAD precursor is administered orally, transmucosally (e.g., nasally), via inhalation or topically. In certain embodiments, the NAD precursor is administered orally. In certain embodiments, the NAD precursor is administered via an injection. In certain embodiments, the NAD precursor is administered transdermally. In certain embodiments, the NAD precursor is formulated as a pill, a powder, a nasal spray or solution, or as an ointment or cream. In certain embodiments, the NAD precursor is in a lipophilic formulation.

In certain embodiments, the NAD precursor is administered via a device. For example, in certain embodiments, the NAD precursor may be coated on or comprised within a device (e.g., a man-made or natural material).

In certain embodiments, the NAD precursor is administered to the female mammal once to three times daily.

In certain embodiments, the methods of the invention may further comprise the administration of a second biologically active agent. In certain embodiments, the second therapeutic agent is useful for modulating the absorption and/or distribution of the NAD precursor (e.g., improving the NAD precursor bioavailability). The second biologically active agent may be administered either simultaneously or sequentially with the NAD precursor. In certain embodiments, the second biologically active agent is administered simultaneously with the NAD precursor. In certain embodiments, a composition (e.g., a pharmaceutical composition) comprising the NAD precursor and the second biologically active agent is administered. In certain embodiments, the NAD precursor and the second biologically active agent are administered sequentially. In certain embodiments, the NAD precursor is administered first and the second biologically active agent is administered second. In certain embodiments, the second biologically active agent is administered first and NAD precursor is administered second.

Certain embodiments of the invention provide a NAD precursor for use in medical therapy.

Certain embodiments of the invention provide a NAD precursor for breast enhancement in a female mammal (e.g., a human).

Certain embodiments of the invention provide the use of a NAD precursor to prepare a medicament for breast enhancement in a female mammal (e.g., a human) in need thereof.

Certain embodiments of the invention provide a NAD precursor for increasing mammary gland mass and/or volume in a female mammal (e.g., a human).

Certain embodiments of the invention provide the use of a NAD precursor to prepare a medicament for increasing mammary gland mass and/or volume in a female mammal (e.g., a human) in need thereof.

Certain embodiments of the invention provide a NAD precursor for promoting mammary gland development in a female mammal (e.g., a human).

Certain embodiments of the invention provide the use of a NAD precursor to prepare a medicament for promoting mammary gland development in a female mammal (e.g., a human) in need thereof.

Certain embodiments of the invention provide a composition (e.g., a pharmaceutical composition) for use in breast enhancement, increasing mammary gland mass and/or volume and/or in promoting mammary gland development in a female mammal (e.g., a human) in need thereof, comprising a NAD precursor, and a carrier (e.g., a pharmaceutically acceptable carrier).

Certain embodiments of the invention provide a kit comprising a NAD precursor and instructions for administering the NAD precursor to a female mammal for breast enhancement, increasing mammary gland mass and/or volume, and/or promoting mammary gland development in the female mammal.

Certain embodiments of the invention provide a kit comprising 1) a composition (e.g., a pharmaceutical composition) comprising a NAD precursor and a carrier (e.g., a pharmaceutically acceptable carrier), wherein the composition is formulated for oral or topical administration; and 2) instructions for orally or topically administering the NAD precursor to a female mammal for breast enhancement, increasing mammary gland mass and/or volume, and/or promoting mammary gland development.

The term "mammal" refers to any mammalian species such as a human, mouse, rat, dog, cat, hamster, guinea pig, rabbit, livestock (e.g., a cow, sheep, horse, pig, chicken, etc.), and the like. Accordingly, in certain embodiments, the mammal is a human, mouse, rat, dog, cat, hamster, guinea pig, rabbit or livestock. In certain embodiments, the mammal is a human.

NAD Precursors

As used herein, the term "NAD precursor" refers to molecules that can be converted/synthesized in vivo into NAD. NAD precursors are known in the art and include, for example, NR and derivatives and analogs thereof (e.g., nicotinoyl ribosides), as well as molecules that can be converted/synthesized in vivo into NR. For example, certain NAD precursors are discussed in WO 2006/116322, WO 2015014722, WO 2015186114, WO 2015186068, WO 2016014927, WO 2016/149277, WO 2016049236, WO 2015066382, U.S. Pat. No. 9,408,834, and Kulikova et al., Journal of Biological Chemistry (2015), 290(45), 27124-27137, which are incorporated by reference herein.

In certain embodiments, the NAD precursor is a compound of formula (I):

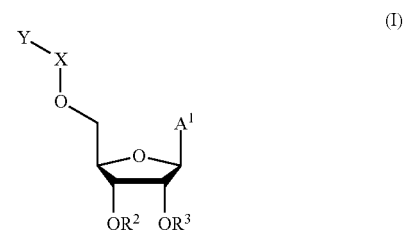

(I)

or a salt thereof (e.g., a pharmaceutically acceptable salt thereof), wherein:

$A^1$ is

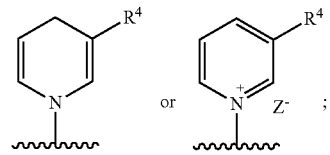

$R^1$ is —COOH, —C(=O)NH$_2$ or —C(=O)OR$^a$;
$R^2$ is H or (C$_1$-C$_3$)alkanoyl;
$R^3$ is H or (C$_1$-C$_3$)alkanoyl;
i) X is absent, —P(=O)(OW)(O—), or —P(=O)(OW)—O—P(=O)(OW)(O—); and
Y is W, or

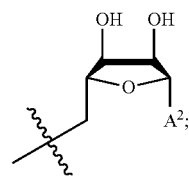

or
ii) X is absent; and Y is (C$_1$-C$_{10}$)alkanoyl;
R$^a$ is (C$_1$-C$_{10}$)alkyl, (C$_2$-C$_{10}$)alkenyl, or aryl, wherein each (C$_1$-C$_{10}$)alkyl, (C$_2$-C$_{10}$)alkenyl and aryl is optionally substituted with one or more groups independently selected from the group consisting of halo, hydroxyl, cyano, (C$_1$-C$_3$)alkoxy, (C$_1$-C$_3$)alkoxycarbonyl, aryl, and (C$_1$-C$_3$)alkanoyloxy;

each W is independently selected from the group consisting of H and pharmaceutically acceptable cations;

A² is

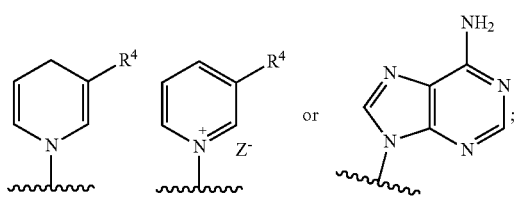

Z is a pharmaceutically acceptable anion;
R⁴ is —COOH, —C(=O)NH₂ or —C(=O)OR$^b$; and
R$^b$ is $(C_1-C_{10})$alkyl, $(C_2-C_{10})$alkenyl, or aryl, wherein each $(C_1-C_{10})$alkyl, $(C_2-C_{10})$alkenyl and aryl is optionally substituted with one or more groups independently selected from the group consisting of halo, hydroxyl, cyano, $(C_1-C_3)$alkoxy, $(C_1-C_3)$alkoxycarbonyl, aryl, and $(C_1-C_3)$alkanoyloxy.

In certain embodiments, R¹ is —COOH or —C(=O)OR$^a$;
In certain embodiments, R¹ is —COOH.
In certain embodiments, R¹ is -C(=O)NH₂.
In certain embodiments, R¹ is not —C(=O)NH₂.
In certain embodiments, R¹ is -C(=O)OR$^a$.
In certain embodiments, R² is H.
In certain embodiments, R² is $(C_1-C_3)$alkanoyl.
In certain embodiments, R² is acyl.
In certain embodiments, R³ is $(C_1-C_3)$alkanoyl.
In certain embodiments, R³ is acyl.
In certain embodiments, X is absent, —P(=O)(OW)(O—), or —P(=O)(OW)—O—P(=O)(OW)(O—); and Y is W or

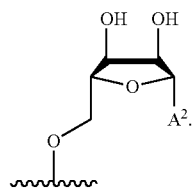

In certain embodiments, Y is

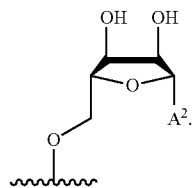

In certain embodiments, X is absent.
In certain embodiments, X is —P(=O)(OW)(O—), or —P(=O)(OW)—O—P(=O)(OW)(O—).
In certain embodiments, X is absent and Y is $(C_1-C_{10})$alkanoyl.
In certain embodiments, Y is acyl.
In certain embodiments, X is not absent and Y is not $(C_1-C_{10})$alkanoyl.
In certain embodiments, R$^a$ is $(C_1-C_{10})$alkyl.
In certain embodiments, each W is H.
In certain embodiments, each W is independently selected from the group consisting pharmaceutically acceptable cations.

In certain embodiments, each W is independently selected from sodium and potassium.

In certain embodiments, A² is

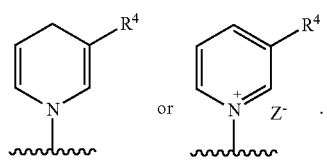

In certain embodiments, A² is

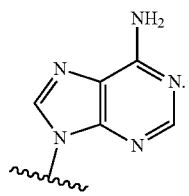

In certain embodiments, Z is chloride.

In one embodiment, the NAD precursor is a compound of formula (I):

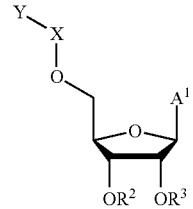

or a salt thereof (e.g., a pharmaceutically acceptable salt), wherein:

A¹ is

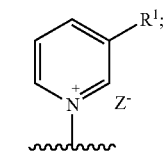

R¹ is —COOH, —C(=O)NH₂ or —C(=O)OR$^a$;
R² is $(C_1-C_3)$alkanoyl;
R³ is $(C_1-C_3)$alkanoyl;
X is absent; and Y is $(C_1-C_{10})$alkanoyl;
R$^a$ is $(C_1-C_{10})$alkyl, $(C_2-C_{10})$alkenyl, or aryl, wherein each $(C_1-C_{10})$alkyl, $(C_2-C_{10})$alkenyl and aryl is optionally substituted with one or more groups independently selected from the group consisting of halo, hydroxyl, cyano, $(C_1-C_3)$alkoxy, $(C_1-C_3)$alkoxycarbonyl, aryl, and $(C_1-C_3)$alkanoyloxy; and
Z is a pharmaceutically acceptable anion.

In one embodiment, the NAD precursor is a compound of formula (I):

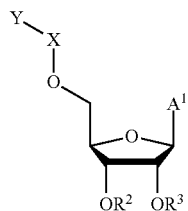
(I)

or a salt thereof (e.g., a pharmaceutically acceptable salt), wherein:

$A^1$ is

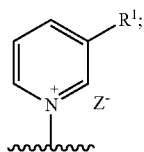

$R^1$ is —C(=O)O$R^a$;
$R^2$ is H or (C$_1$-C$_3$)alkanoyl;
$R^3$ is H or (C$_1$-C$_3$)alkanoyl;
X is absent;
Y is W or (C$_1$-C$_{10}$)alkanoyl;
$R^a$ is (C$_1$-C$_{10}$)alkyl, (C$_2$-C$_{10}$)alkenyl, or aryl, wherein each (C$_1$-C$_{10}$)alkyl, (C$_2$-C$_{10}$)alkenyl and aryl is optionally substituted with one or more groups independently selected from the group consisting of halo, hydroxyl, cyano, (C$_1$-C$_3$)alkoxy, (C$_1$-C$_3$)alkoxycarbonyl, aryl, and (C$_1$-C$_3$)alkanoyloxy;
each W is independently selected from the group consisting of H and pharmaceutically acceptable cations; and
Z is a pharmaceutically acceptable anion.

In certain embodiments, the compound of formula (I) is selected from the group consisting of:

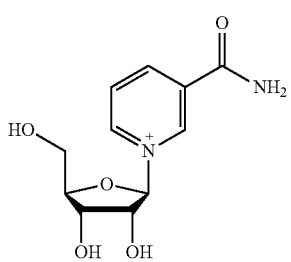
Nicotinamide riboside (NR)

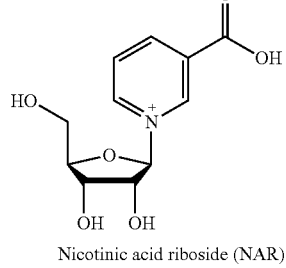
Nicotinic acid riboside (NAR)

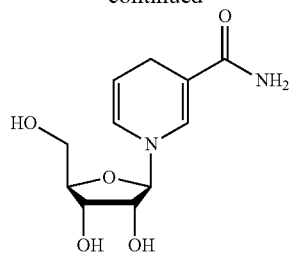
1,4-dihydronicotinamide riboside (NRH)

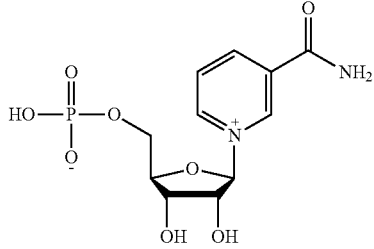
Nicotinamide mononucleotide (NMN)

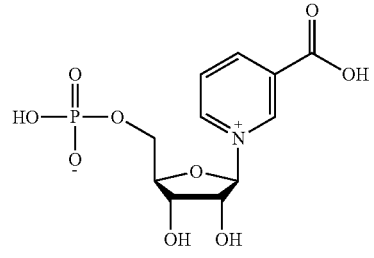
Nicotinic acid mononucleotide (NAMN)

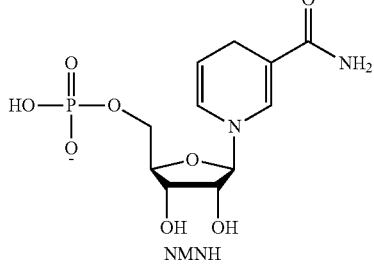
NMNH

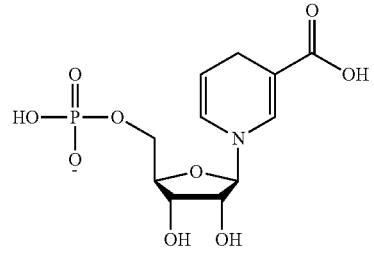
NAMNH

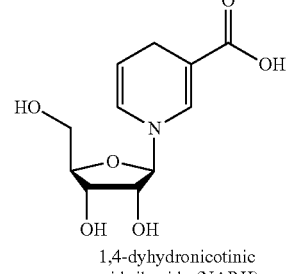
1,4-dyhydronicotinic acid riboside (NARH)

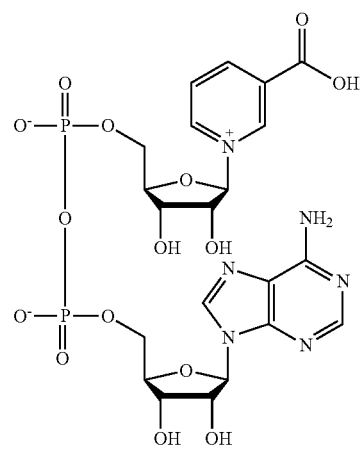
Nicotinamide Adenine Dinucleotide (NAD)
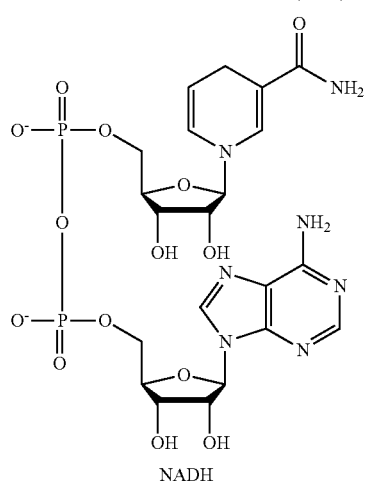
NADH
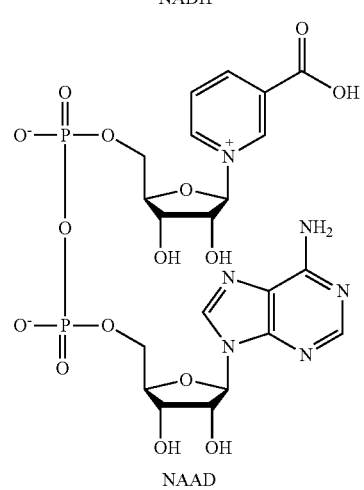
NAAD
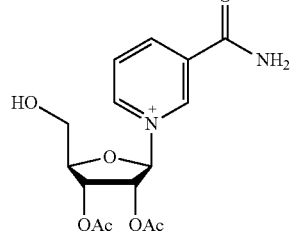
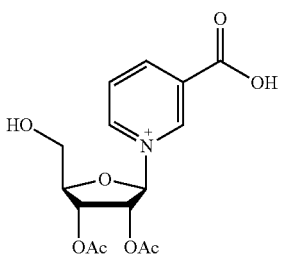
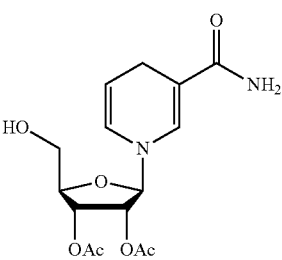
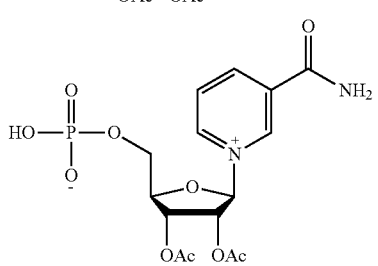
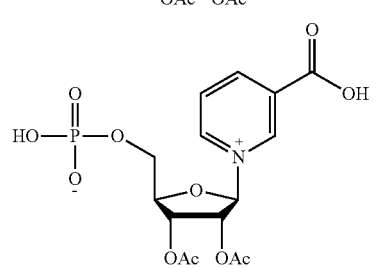
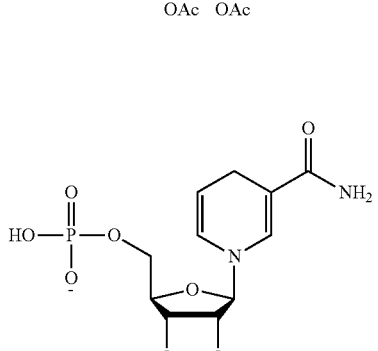
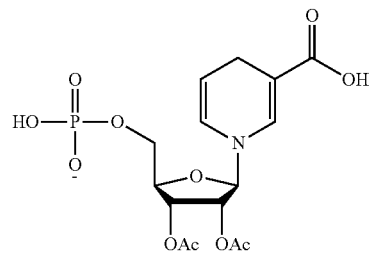

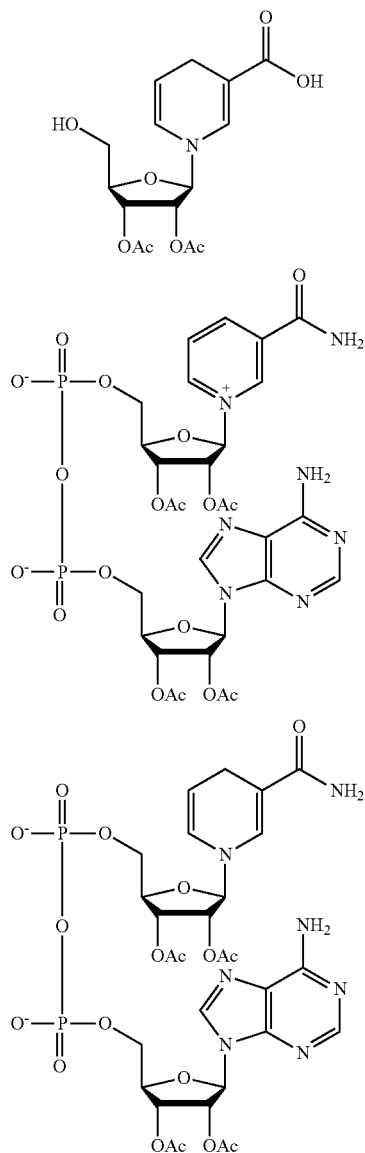
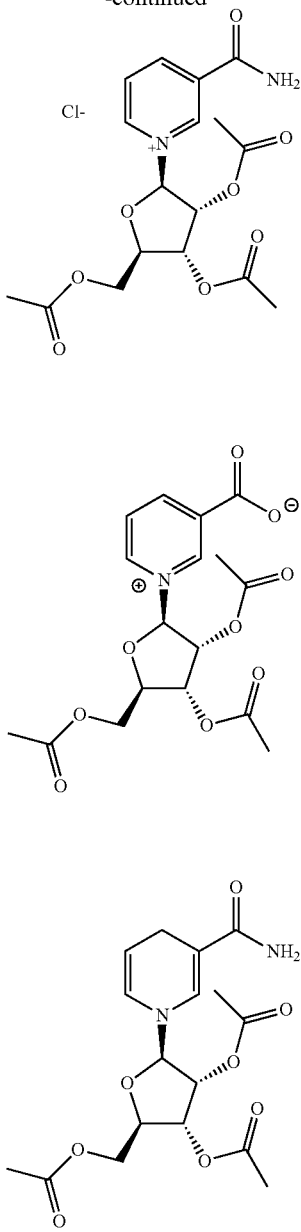
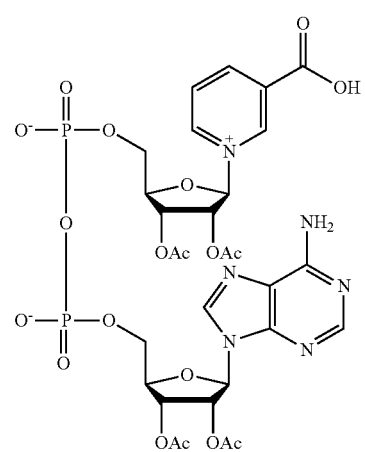
and salts thereof (e.g., pharmaceutically acceptable salts thereof).
In certain embodiments, the NAD precursor is NR:
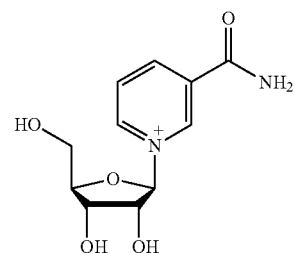
or a salt thereof (e.g., a pharmaceutically acceptable salt thereof).

In certain embodiments, the NAD precursor is NR chloride:

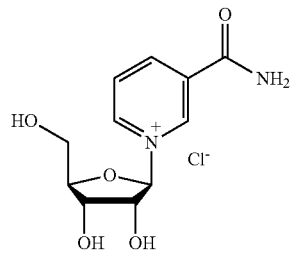

or a salt thereof (e.g., a pharmaceutically acceptable salt thereof).

In certain embodiments, the NAD precursor is not NAMNH. In certain embodiments, the NAD precursor is not NARH.

The following definitions are used, unless otherwise described: halo is fluoro, chloro, bromo, or iodo. Alkyl, alkoxy, and alkenyl etc. denote both straight and branched groups; but reference to an individual radical such as propyl embraces only the straight chain radical, a branched chain isomer such as isopropyl being specifically referred to. Aryl denotes a phenyl radical or an ortho-fused bicyclic carbocyclic radical having about nine to ten ring atoms in which at least one ring is aromatic.

Specific values listed below for radicals, substituents, and ranges, are for illustration only; they do not exclude other defined values or other values within defined ranges for the radicals and substituents.

Specifically, $(C_1-C_{10})$alkyl can be methyl, ethyl, propyl, isopropyl, butyl, iso-butyl, sec-butyl, pentyl, 3-pentyl, hexyl, heptyl, octyl, nonyl, or decyl; $(C_1-C_3)$alkoxy can be methoxy, ethoxy, or propoxy; $(C_2-C_{10})$alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, 5-hexenyl; 1-heptenyl, 1-octenyl, 1-nonenyl, or 1-decenyl; $(C_1-C_3)$alkoxycarbonyl can be methoxycarbonyl, ethoxycarbonyl, or propoxycarbonyl, $(C_1-C_3)$alkanoyloxy can be formyloxy, acetoxy, or propanoyloxy; and aryl can be phenyl, indenyl, or naphthyl.

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

It is understood that compounds of formula (I) that include both a positively charged nitrogen (e.g., a pyridinium nitrogen atom or quaternary nitrogen atom) and a carboxylic acid group may exist as a single molecule that possesses both a positive charge and a negative charge (e.g. a zwitterion). Accordingly, as used herein, the term "pharmaceutically acceptable salt" includes such zwitterions. For example, the compound 100 below represents a pharmaceutically acceptable salt of the compound 101.

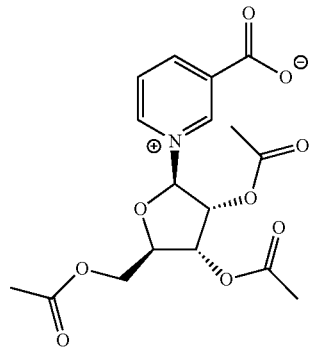

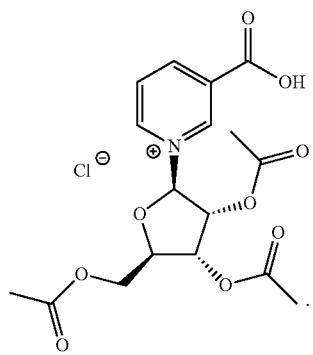

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Pharmaceutically acceptable cations are well known in the art and include, sodium, potassium, magnesium and calcium.

Pharmaceutically acceptable anions are well known in the art and include, chloride, bromide, iodide, tosylate, methanesulfonate, acetate, citrate, malonate, tartarate, succinate, benzoate, ascorbate, α-ketoglutarate, and α-glycerophosphate.

Administration

A compound described herein for use in the invention can be formulated as a composition (e.g., a pharmaceutical composition) and administered to a mammalian host, such as a human subject (e.g., a woman or transgender woman) in a variety of forms adapted to the chosen route of administration, i.e., orally or parenterally, by intravenous, intramuscular, topical (e.g., transdermal, transmucosal), inhalation or subcutaneous routes.

Thus, the present compounds may be systemically administered, e.g., orally (e.g., added to drinking water), in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the compound may be combined with one or more excipients and used in the form of ingestible tablets, buccal tablets, troches, capsules, elixirs, suspensions, syrups, wafers, and the like. Such compositions and preparations should contain at least 0.1% of the compound. The percentage of the compositions and preparations may, of course, be varied and may conveniently be between about 2 to about 60% of the weight of a given unit dosage form. The amount of compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the compound may be incorporated into sustained-release preparations and devices.

The compound may also be administered intravenously or intraperitoneally by infusion or injection. Solutions of the compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The compounds may be conveniently formulated in unit dosage form. In one embodiment, the invention provides a composition comprising a compound formulated in such a unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

A NAD precursor can also be administered in combination with other therapeutic or biologically active agents, for example, other agents that are useful for modulating the absorption and/or distribution of the NAD precursor (e.g., improving the NAD precursor bioavailability, such as oral, nasal or topical bioavailability). Accordingly, in one embodiment the invention also provides a composition comprising an NAD precursor, at least one other therapeutic or biologically active agent, and a pharmaceutically acceptable diluent or carrier. The invention also provides a kit comprising a NAD precursor, at least one other therapeutic or biologically active agent, packaging material, and instructions for administering the NAD precursor and the other therapeutic/biologically active agent or agents to a female mammal for breast enhancement or for the promotion of mammary gland development.

The invention will now be illustrated by the following non-limiting Examples.

Example 1

As described herein, a series of experiments were performed to examine the effect of nicotinamide riboside (NR) on mammary tissue. It was determined that the provision of NR in the diet of female mice and female rats promoted mammary development (e.g., increases mammary gland tissue weight). This effect was observed in female and not male rodents. Adult females, whether virginal or pregnant, fed a diet supplemented with NR, exhibited an increase in fat pad formation, epithelial branching, alveolar and lobule development of their mammary glands. It was also determined that NR supplementation leads to development of beige or brown fat and that NR changes the fat composition of the mammary gland of female rodents. These experiments show the unanticipated and potentially value effect of supplementing females with NR or other NAD precursors.

NR Increases Mammary Size of Lactating Female Mice

Figure 1A:
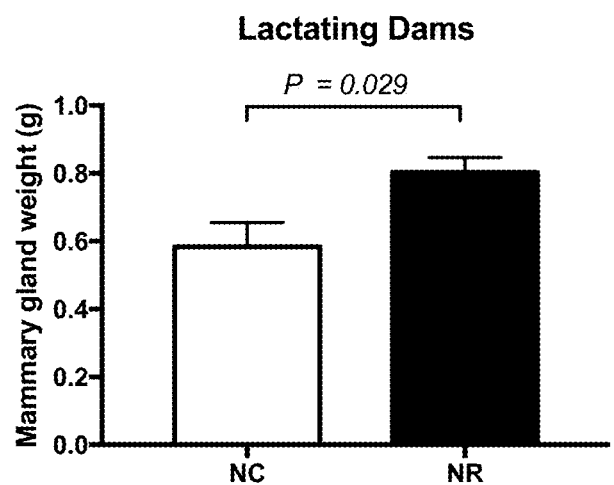
FIGS. 1A-B. NR increases the mass of mammary glands of lactating mice. C57BL/6 female mice were fed normal chow (NC) diet and mated to a C57BL/6 male. After gestation and birth, females remained on NC or were on or a diet supplemented with 3 g/kg nicotinamide riboside chloride (NR). At day 14, the females were sacrificed and mammary glands 1-5 were removed for analysis.
Figure 1B:
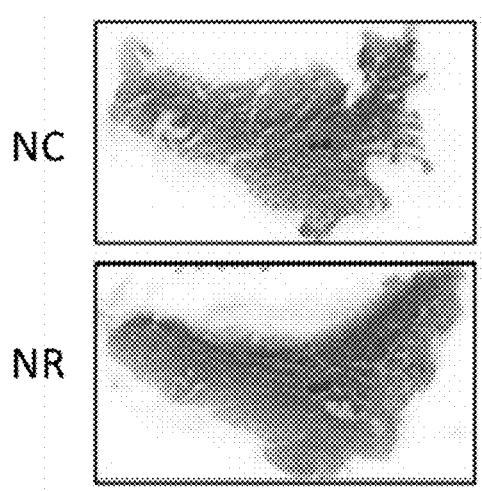
Figure 2A:
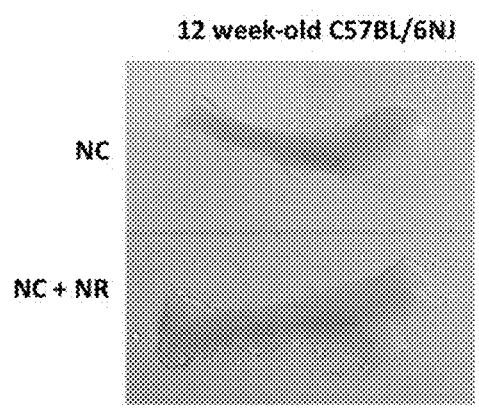
FIGS. 2A-E. NR oral supplementation promotes mammary gland development in virgin female mice (non-lactating females).
Figure 2B:
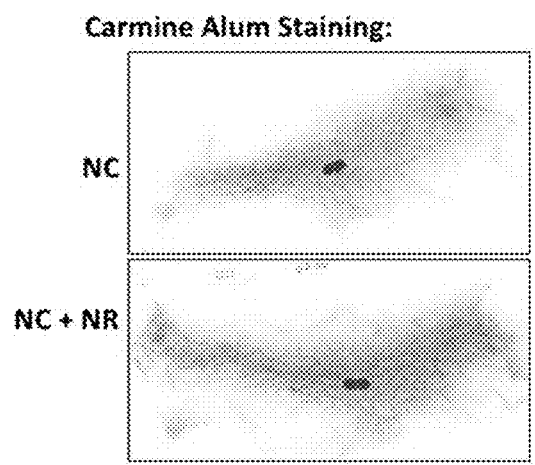
Figure 2C:
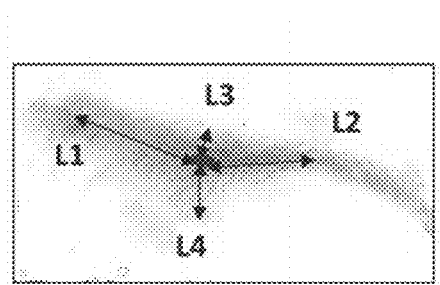
Figure 2D:
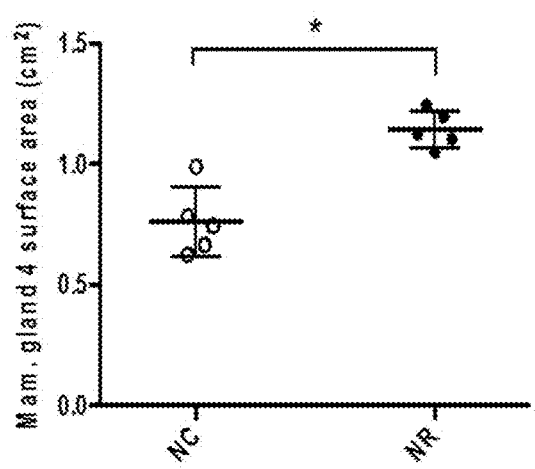
Figure 2E:
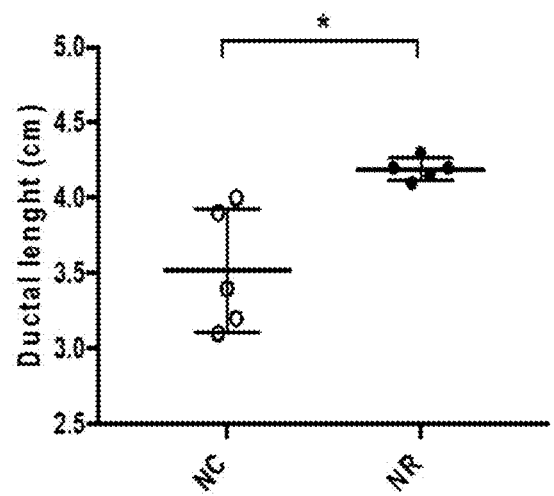

The data are based on a trial with female C57BL/6N mice raised in 12 hour light:dark cycles on Teklad 2920X chow (NC). It was asked whether addition of NR chloride (3 g/kg of chow) to the diet of female mice would augment mammary tissue. Accordingly, for 12 weeks prior to mating with a single C57BL/6N male, females were on either NC (n=4) or NC+NR (n=4). Females were maintained on the same diet for 14 days post-partum. As shown in FIGS. 1A-B, the lactating dams on NR have more mammary tissue than those on normal chow.

NR Increases the Mammary Size of Virgin Female Mice

A similar experiment conducted on virgin mice, not exposed to males, also showed mammary gland development. Specifically, a significant increase of the subcutaneous adipose tissue and epithelial duct branching contributing to the composition of the breast was observed (FIGS. 2A-E).

NR Increases the Mammary Size of Virgin Female Rats

Figure 3A:
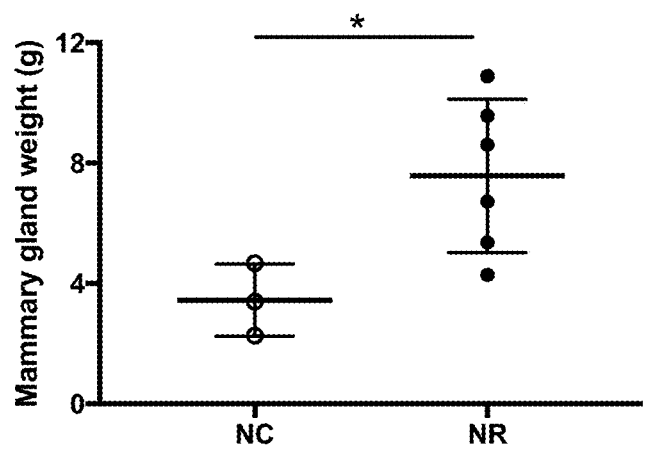
FIGS. 3A-C. NR increases the mass of mammary gland #4 and #5 and brown adipose tissue (BAT) of female rats. Adipose tissues of female rats on normal chow diet (NC) or normal chow with nicotinamide riboside (NR).
Figure 3B:
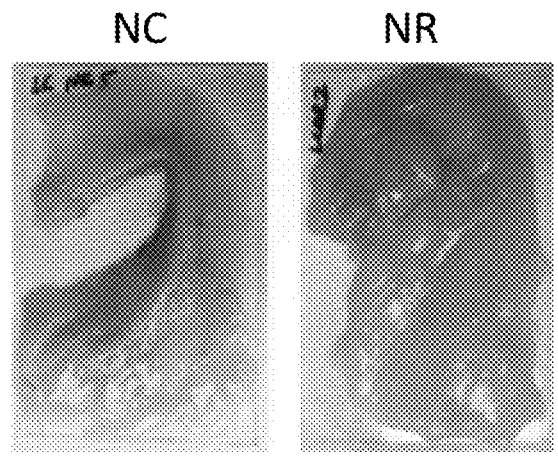
Figure 3C:
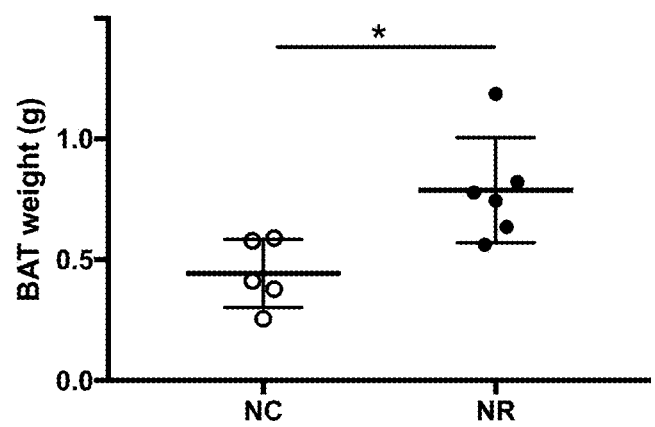

To determine if the effect of NR on females was a mouse-specific phenomenon, additional experiments were performed. Specifically, virgin female rats were fed either NC or NR diets prior to dissection. As shown in FIGS. 3A-C, on the basis of the mass of subcutaneous white adipose tissue, total mass and brown adipose tissue, NR increased the size of mammary tissues in rats.

NR Increases Mammary Size of Male but not Female Mice

Figure 4:
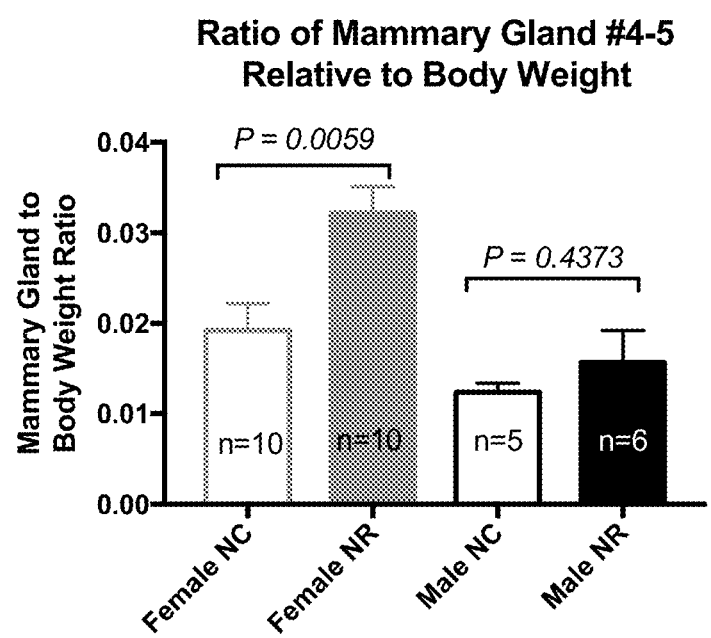
FIG. 4. NR increases mammary gland tissue weight of female but not male mice. Eight month-old mice were put on NC or NR diet for six weeks. Mammary glands #4 and 5 were measured and plotted by normalizing to the body weight of each mouse. NR-supplemented females have more mammary gland in comparison to the NC group. Male mice supplemented with NR showed no significant increase in mammary tissue weight.

In FIG. 4, eight month-old mice were put on normal chow (NC) or NC+NR (NR) diets for six weeks. Mammary glands #4 and 5 were measured and plotted by normalizing to the body weight of each mouse. As shown earlier, NR-supplemented females have more mammary gland tissue in comparison to the NC group. In contrast, male mice supplemented with NR showed no significant increase in mammary tissue weight.

NR Alters the Fat Composition of the Mammary Gland of Virgin Female Mice

Eight month-old female mice were on NC or NR diet for six weeks. Mammary glands #4-5 were isolated, fixed, stained with Carmine/Alum stain and subjected to an extraction with xylene to remove fat. After 1 week of incubation in xylene, mammary glands from NR-fed mice have more fat remaining. Accordingly, it was determined that NR supplementation changes the fat composition of the mammary gland of female mice (see, FIGS. 5A-5B).

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method comprising: a) increasing the firmness of a female breast, b) improving the shape of a female breast, c) increasing the size of a female breast, d) increasing mammary gland mass and/or volume, or e) promoting mammary gland development in a female mammal, by administering to the mammal, a compound of formula (I):

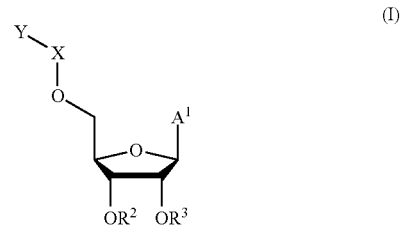

or a pharmaceutically acceptable salt thereof, wherein:
$A^1$ is

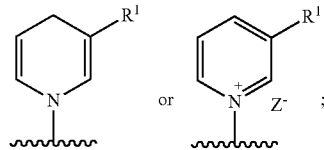

$R^1$ is —COOH, —C(=O)NH$_2$ or —C(=O)OR$^a$;
$R^2$ is H or (C$_1$-C$_3$)alkanoyl;
$R^3$ is H or (C$_1$-C$_3$)alkanoyl;
i) X is absent, —P(=O)(OW)(O—), or —P(=O)(OW)—O—P(=O)(OW)(O—); and
Y is W, or

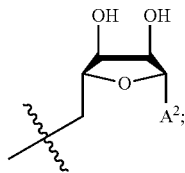

or ii) X is absent and Y is (C$_1$-C$_{10}$)alkanoyl;
$R^a$ is (C$_1$-C$_{10}$)alkyl, (C$_2$-C$_{10}$)alkenyl, or aryl, wherein each (C$_1$-C$_{10}$)alkyl, (C$_2$-C$_{10}$)alkenyl and aryl is optionally substitutes with one or more groups independently selected from the group consisting of halo, hydroxyl, cyano, (C$_1$-C$_3$)alkoxy, (C$_1$-C$_3$)alkoxycarbonyl, aryl, and (C$_1$-C$_3$)alkanoyloxy;
each W is independently selected from the group consisting of H and pharmaceutically acceptable cations;

21

$A^2$ is

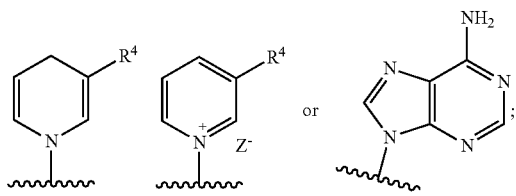

Z is a pharmaceutically acceptable anion;
$R^4$ is —COOH, —C(=O)NH$_2$ or —C(=O)OR$^b$; and
$R^b$ is (C$_1$-C$_{10}$)alkyl, (C$_2$-C$_{10}$)alkenyl, or aryl, wherein each (C$_1$-C$_{10}$)alkyl, (C$_2$-C$_{10}$)alkenyl and aryl is optionally substitutes with one or more groups independently selected from the group consisting of halo, hydroxyl, cyano, (C$_1$-C$_3$)alkoxy, (C$_1$-C$_3$)alkoxycarbonyl, aryl, and (C$_1$-C$_3$)alkanoyloxy;

wherein the firmness, shape, or size of the female breast is increased by at least about 1%; and wherein the compound or the pharmaceutically acceptable salt thereof is administered orally, transmucosally, via inhalation, or topically.

2. A method comprising: a) increasing the firmness of a female breast, b) improving the shape of a female breast, c) increasing the size of a female breast, d) increasing mammary gland mass and/or volume, or e) promoting mammary gland development in a female mammal, by administering to the mammal, a compound of formula (I):

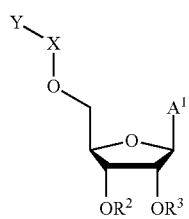

(I)

or a pharmaceutically acceptable salt thereof, wherein:

$A^1$ is

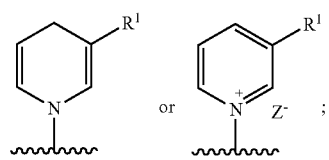

$R^1$ is —COOH, —C(=O)NH$_2$ or —C(=O)OR$^a$;
$R^2$ is H or (C$_1$-C$_3$)alkanoyl;
$R^3$ is H or (C$_1$-C$_3$)alkanoyl;
iii) X is absent, —P(=O)(OW)(O—), or —P(=O)(OW)—O—P(=O)(OW)(O—); and

22

Y is W, or

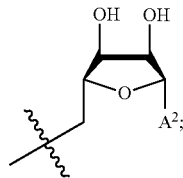

or iv) X is absent and Y is (C$_1$-C$_{10}$)alkanoyl;
$R^a$ is (C$_1$-C$_{10}$)alkyl, (C$_2$-C$_{10}$)alkenyl, or aryl, wherein each (C$_1$-C$_{10}$)alkyl, (C$_2$-C$_{10}$)alkenyl and aryl is optionally substitutes with one or more groups independently selected from the group consisting of halo, hydroxyl, cyano, (C$_1$-C$_3$)alkoxy, (C$_1$-C$_3$)alkoxycarbonyl, aryl, and (C$_1$-C$_3$)alkanoyloxy;

each W is independently selected from the group consisting of H and pharmaceutically acceptable cations;

$A^2$ is

Z is a pharmaceutically acceptable anion;
$R^4$ is —COOH, —C(=O)NH$_2$ or —C(=O)OR$^b$; and
$R^b$ is (C$_1$-C$_{10}$)alkyl, (C$_2$-C$_{10}$)alkenyl, or aryl, wherein each (C$_1$-C$_{10}$)alkyl, (C$_2$-C$_{10}$)alkenyl and aryl is optionally substitutes with one or more groups independently selected from the group consisting of halo, hydroxyl, cyano, (C$_1$-C$_3$)alkoxy, (C$_1$-C$_3$)alkoxycarbonyl, aryl, and (C$_1$-C$_3$)alkanoyloxy;

wherein the firmness, shape, or size of the female breast is increased by at least about 1%; and by administering a second biologically active agent useful for modulating the absorption and/or distribution of the compound or the pharmaceutically acceptable salt thereof.

3. A method comprising: a) increasing the firmness of a female breast, b) improving the shape of a female breast, c) increasing the size of a female breast, d) increasing mammary gland mass and/or volume, or e) promoting mammary gland development in a female mammal, by administering to the mammal, a compound of formula (I):

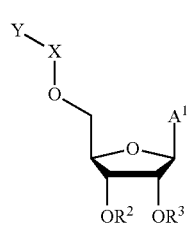

(I)

or a pharmaceutically acceptable salt thereof, wherein:
A¹ is

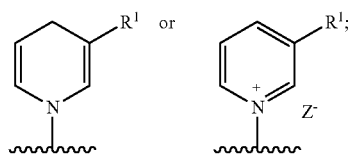

R¹ is —COOH, —C(=O)NH₂ or —C(=O)OR$^a$;
R² is H or (C₁-C₃)alkanoyl;
R³ is H or (C₁-C₃)alkanoyl;
X is absent and Y is (C₁-C₁₀)alkanoyl;
R$^a$ is (C₁-C₁₀)alkyl, (C₂-C₁₀)alkenyl, or aryl, wherein each (C₁-C₁₀)alkyl, (C₂-C₁₀)alkenyl and aryl is optionally substitutes with one or more groups independently selected from the group consisting of halo, hydroxyl, cyano, (C₁-C₃)alkoxy, (C₁-C₃)alkoxycarbonyl, aryl, and (C₁-C₃)alkanoyloxy;
A² is

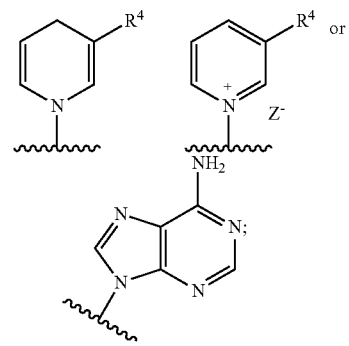

Z is a pharmaceutically acceptable anion;
R⁴ is —COOH, —C(=O)NH₂ or —C(=O)OR$^b$; and
R$^b$ is (C₁-C₁₀)alkyl, (C₂-C₁₀)alkenyl, or aryl, wherein each (C₁-C₁₀)alkyl, (C₂-C₁₀)alkenyl and aryl is optionally substitutes with one or more groups independently selected from the group consisting of halo, hydroxyl, cyano, (C₁-C₃)alkoxy, (C₁-C₃)alkoxycarbonyl, aryl, and (C₁-C₃)alkanoyloxy;
wherein the firmness, shape, or size of the female breast is increased by at least about 1%.

4. A method comprising: a) increasing the firmness of a female breast, b) improving the shape of a female breast, c) increasing the size of a female breast, d) increasing mammary gland mass and/or volume, or e) promoting mammary gland development in a female mammal, by administering to the mammal, a compound of formula (I):

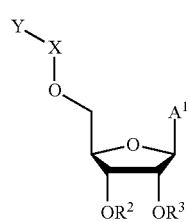

(I)

or a pharmaceutically acceptable salt thereof, wherein:
A¹ is

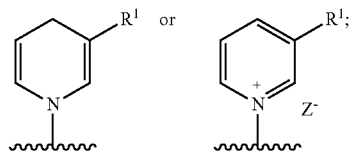

R¹ is —COOH, —C(=O)NH₂ or —C(=O)OR$^a$;
R² is H or (C₁-C₃)alkanoyl;
R³ is H or (C₁-C₃)alkanoyl;
i) X is absent, —P(=O)(OW)(O—), or —P(=O)(OW)—O—P(=O)(OW)(O—); and
Y is W, or

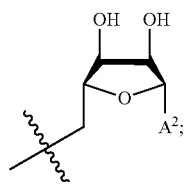

ii) X is absent and Y is (C₁-C₁₀)alkanoyl;
R$^a$ is (C₁-C₁₀)alkyl, (C₂-C₁₀)alkenyl, or aryl, wherein each (C₁-C₁₀)alkyl, (C₂-C₁₀)alkenyl and aryl is optionally substitutes with one or more groups independently selected from the group consisting of halo, hydroxyl, cyano, (C₁-C₃)alkoxy, (C₁-C₃)alkoxycarbonyl, aryl, and (C₁-C₃)alkanoyloxy;
each W is independently selected from the group consisting of pharmaceutically acceptable cations;
A² is

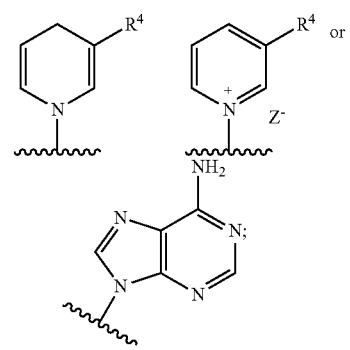

Z is a pharmaceutically acceptable anion;

$R^4$ is —COOH, —C(=O)NH$_2$ or —C(=O)OR$^b$; and $R^b$ is (C$_1$-C$_{10}$)alkyl, (C$_2$-C$_{10}$)alkenyl, or aryl, wherein each (C$_1$-C$_{10}$)alkyl, (C$_2$-C$_{10}$)alkenyl and aryl is optionally substitutes with one or more groups independently selected from the group consisting of halo, hydroxyl, cyano, (C$_1$-C$_3$)alkoxy, (C$_1$-C$_3$)alkoxycarbonyl, aryl, and (C$_1$-C$_3$)alkanoyloxy, wherein the firmness, shape, or size of the female breast is increased by at least about 1%.

5. The method of claim 4, wherein each W is independently selected from sodium and potassium.

6. A method comprising: a) increasing the firmness of a female breast, b) improving the shape of a female breast, c) increasing the size of a female breast, d) increasing mammary gland mass and/or volume, or e) promoting mammary gland development in a female mammal, by administering to the mammal, a compound of formula (I):

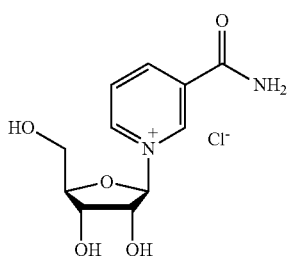

or a pharmaceutically acceptable salt thereof; wherein the firmness, shape, or size of the female breast is increased by at least about 1%.

7. A kit comprising:

1) a composition comprising a compound of formula (I):

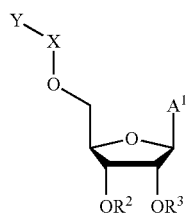

or a pharmaceutically acceptable salt thereof, wherein:

A$^1$ is

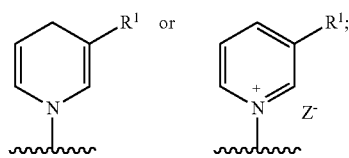

$R^1$ is —COOH, —C(=O)NH$_2$ or —C(=O)OR$^a$;

$R^2$ is H or (C$_1$-C$_3$)alkanoyl;

$R^3$ is H or (C$_1$-C$_3$)alkanoyl;

v) X is absent, —P(=O)(OW)(O—), or —P(=O)(OW)—O—P(=O)(OW)(O—); and

Y is W, or

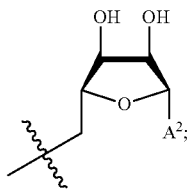

or vi) X is absent and Y is (C$_1$-C$_{10}$)alkanoyl;

$R^a$ is (C$_1$-C$_{10}$)alkyl, (C$_2$-C$_{10}$)alkenyl, or aryl, wherein each (C$_1$-C$_{10}$)alkyl, (C$_2$-C$_{10}$)alkenyl and aryl is optionally substitutes with one or more groups independently selected from the group consisting of halo, hydroxyl, cyano, (C$_1$-C$_3$)alkoxy, (C$_1$-C$_3$)alkoxycarbonyl, aryl, and (C$_1$-C$_3$)alkanoyloxy;

each W is independently selected from the group consisting of H and pharmaceutically acceptable cations;

A$^2$ is

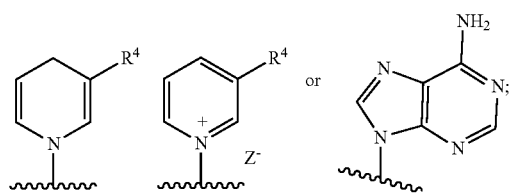

Z is a pharmaceutically acceptable anion;

$R^4$ is —COOH, —C(=O)NH$_2$ or —C(=O)OR$^b$; and $R^b$ is (C$_1$-C$_{10}$)alkyl, (C$_2$-C$_{10}$)alkenyl, or aryl, wherein each (C$_1$-C$_{10}$)alkyl, (C$_2$-C$_{10}$)alkenyl and aryl is optionally substitutes with one or more groups independently selected from the group consisting of halo, hydroxyl, cyano, (C$_1$-C$_3$)alkoxy, (C$_1$-C$_3$)alkoxycarbonyl, aryl, and (C$_1$-C$_3$)alkanoyloxy; and a carrier, wherein the composition is formulated for oral or topical administration; and 2) instructions for orally or topically administering the composition to a female mammal for: a) increasing the firmness of a female breast, b) improving the shape of a female breast, c) increasing the size of a female breast, d) increasing mammary gland mass and/or volume, or e) promoting mammary gland development in a female mammal.

8. A composition comprising, a compound of formula (I):

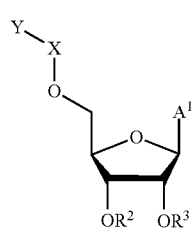

or a pharmaceutically acceptable salt thereof, wherein:
A¹ is

R¹ is —COOH, —C(=O)NH₂ or —C(=O)OR$^a$;
R² is H or (C₁-C₃)alkanoyl;
R³ is H or (C₁-C₃)alkanoyl;
i) X is absent, —P(=O)(OW)(O—), or —P(=O)(OW)—O—P(=O)(OW)(O—); and
Y is W, or or
ii) X is absent and Y is (C₁-C₁₀)alkanoyl;
R$^a$ is (C₁-C₁₀)alkyl, (C₂-C₁₀)alkenyl, or aryl, wherein each (C₁-C₁₀)alkyl, (C₂-C₁₀)alkenyl and aryl is optionally substitutes with one or more groups independently selected from the group consisting of halo, hydroxyl, cyano, (C₁-C₃)alkoxy, (C₁-C₃)alkoxycarbonyl, aryl, and (C₁-C₃)alkanoyloxy;
each W is independently selected from the group consisting of H and pharmaceutically acceptable cations;
A² is Z is a pharmaceutically acceptable anion;
R⁴ is —COOH, —C(=O)NH₂ or —C(=O)OR$^b$; and
R$^b$ is (C₁-C₁₀)alkyl, (C₂-C₁₀)alkenyl, or aryl, wherein each (C₁-C₁₀)alkyl, (C₂-C₁₀)alkenyl and aryl is optionally substitutes with one or more groups independently selected from the group consisting of halo, hydroxyl, cyano, (C₁-C₃)alkoxy, (C₁-C₃)alkoxycarbonyl, aryl, and (C₁-C₃)alkanoyloxy; and a carrier, wherein the composition is formulated for oral or topical administration.

9. A method comprising: a) increasing the firmness of a female breast, b) improving the shape of a female breast, c) increasing the size of a female breast, d) increasing mammary gland mass and/or volume, or e) promoting mammary gland development in a female mammal, by administering to the mammal, a compound of formula (I):

or a pharmaceutically acceptable salt thereof, wherein:
A¹ is

R¹ is —COOH, —C(=O)NH₂ or —C(=O)OR$^a$;
R² is H or (C₁-C₃)alkanoyl;
R³ is H or (C₁-C₃)alkanoyl;
vii) X is absent, —P(=O)(OW)(O—), or —P(=O)(OW)—O—P(=O)(OW)(O—); and
Y is W, or or
viii) X is absent and Y is (C₁-C₁₀)alkanoyl;
R$^a$ is (C₁-C₁₀)alkyl, (C₂-C₁₀)alkenyl, or aryl, wherein each (C₁-C₁₀)alkyl, (C₂-C₁₀)alkenyl and aryl is optionally substitutes with one or more groups independently selected from the group consisting of halo, hydroxyl, cyano, (C₁-C₃)alkoxy, (C₁-C₃)alkoxycarbonyl, aryl, and (C₁-C₃)alkanoyloxy;
each W is independently selected from the group consisting of H and pharmaceutically acceptable cations;
A² is Z is a pharmaceutically acceptable anion;
R⁴ is —COOH, —C(=O)NH₂ or —C(=O)OR$^b$; and
R$^b$ is (C₁-C₁₀)alkyl, (C₂-C₁₀)alkenyl, or aryl, wherein each (C₁-C₁₀)alkyl, (C₂-C₁₀)alkenyl and aryl is optionally substitutes with one or more groups independently selected from the group consisting of halo, hydroxyl, cyano, $(C_1-C_3)$alkoxy, $(C_1-C_3)$alkoxycarbonyl, aryl, and $(C_1-C_3)$alkanoyloxy;

wherein the firmness, shape, or size of the female breast is increased by at least about 1%; and wherein the compound of formula (I) or the pharmaceutically acceptable salt thereof is administered in a dose of about 3-5 g per day.

10. A method comprising: a) increasing the firmness of a female breast, b) improving the shape of a female breast, c) increasing the size of a female breast, d) increasing mammary gland mass and/or volume, or e) promoting mammary gland development in a female mammal, by administering to the mammal, a compound of formula (I):

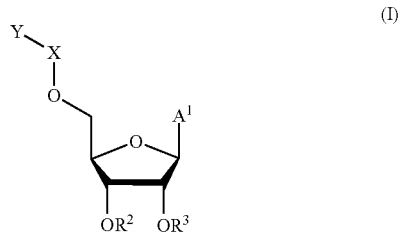

or a pharmaceutically acceptable salt thereof, wherein:
$A^1$ is

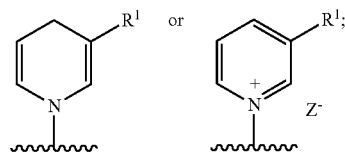

$R^1$ is —COOH, —C(=O)NH$_2$ or —C(=O)OR$^a$;
$R^2$ is H or $(C_1-C_3)$alkanoyl;
$R^3$ is H or $(C_1-C_3)$alkanoyl;
i) X is absent, —P(=O)(OW)(O—), or —P(=O)(OW)—O—P(=O)(OW)(O—); and
Y is W, or

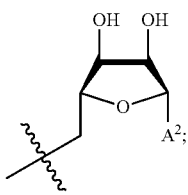

or
ii) X is absent and Y is $(C_1-C_{10})$alkanoyl;

$R^a$ is $(C_1-C_{10})$alkyl, $(C_2-C_{10})$alkenyl, or aryl, wherein each $(C_1-C_{10})$alkyl, $(C_2-C_{10})$alkenyl and aryl is optionally substitutes with one or more groups independently selected from the group consisting of halo, hydroxyl, cyano, $(C_1-C_3)$alkoxy, $(C_1-C_3)$alkoxycarbonyl, aryl, and $(C_1-C_3)$alkanoyloxy;

each W is independently selected from the group consisting of H and pharmaceutically acceptable cations;

$A^2$ is

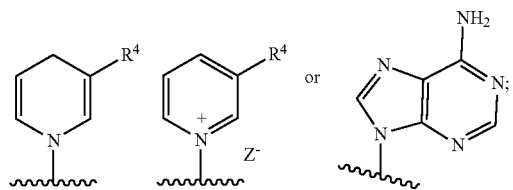

Z is a pharmaceutically acceptable anion;
$R^4$ is —COOH, —C(=O)NH$_2$ or —C(=O)OR$^b$; and
$R^b$ is $(C_1-C_{10})$alkyl, $(C_2-C_{10})$alkenyl, or aryl, wherein each $(C_1-C_{10})$alkyl, $(C_2-C_{10})$alkenyl and aryl is optionally substitutes with one or more groups independently selected from the group consisting of halo, hydroxyl, cyano, $(C_1-C_3)$alkoxy, $(C_1-C_3)$alkoxycarbonyl, aryl, and $(C_1-C_3)$alkanoyloxy;

wherein the firmness, shape, or size of the female breast is increased by at least about 1%; and wherein the compound of formula (I) or the pharmaceutically acceptable salt thereof is administered over at least about 6 weeks.

11. A method comprising: increasing the size of a human female breast by at least about 1% in a human female in need thereof, by administering to the human female, a compound of formula (I):

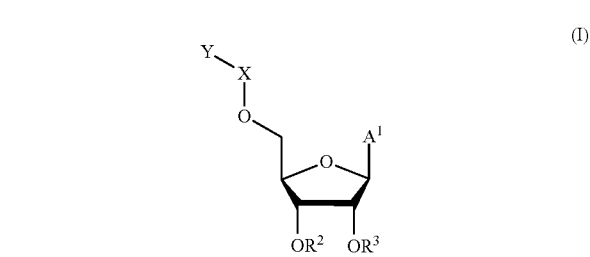

or a pharmaceutically acceptable salt thereof, wherein:
$A^1$ is

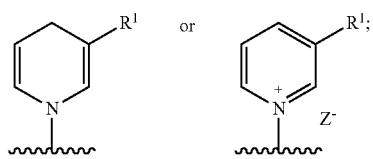

$R^1$ is —COOH, —C(=O)NH$_2$ or —C(=O)OR$^a$;
$R^2$ is H or $(C_1-C_3)$alkanoyl;
$R^3$ is H or $(C_1-C_3)$alkanoyl;
i) X is absent, —P(=O)(OW)(O—), or —P(=O)(OW)—O—P(=O)(OW)(O—); and
Y is W, or

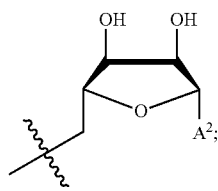

or ii) X is absent and Y is (C$_1$-C$_{10}$)alkanoyl;

R$^a$ is (C$_1$-C$_{10}$)alkyl, (C$_2$-C$_{10}$)alkenyl, or aryl, wherein each (C$_1$-C$_{10}$)alkyl, (C$_2$-C$_{10}$)alkenyl and aryl is optionally substitutes with one or more groups independently selected from the group consisting of halo, hydroxyl, cyano, (C$_1$-C$_3$)alkoxy, (C$_1$-C$_3$)alkoxycarbonyl, aryl, and (C$_1$-C$_3$)alkanoyloxy;

each W is independently selected from the group consisting of H and pharmaceutically acceptable cations;

A$^2$ is

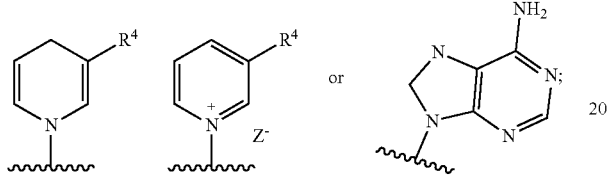

Z is a pharmaceutically acceptable anion;

R$^4$ is —COOH, —C(=O)NH$_2$ or —C(=O)OR$^b$; and

R$^b$ is (C$_1$-C$_{10}$)alkyl, (C$_2$-C$_{10}$)alkenyl, or aryl, wherein each (C$_1$-C$_{10}$)alkyl, (C$_2$-C$_{10}$)alkenyl and aryl is optionally substitutes with one or more groups independently selected from the group consisting of halo, hydroxyl, cyano, (C$_1$-C$_3$)alkoxy, (C$_1$-C$_3$)alkoxycarbonyl, aryl, and (C$_1$-C$_3$)alkanoyloxy.

12. A method comprising: increasing mammary gland mass and/or volume in a human female in need thereof, by administering to the human female, a compound of formula (I):

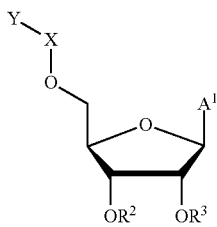

or a pharmaceutically acceptable salt thereof, wherein:

A$^1$ is

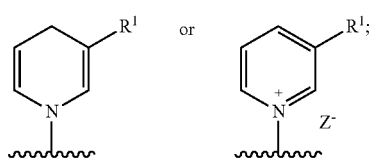

R$^1$ is —COOH, —C(=O)NH$_2$ or —C(=O)OR$^a$;

R$^2$ is H or (C$_1$-C$_3$)alkanoyl;

R$^3$ is H or (C$_1$-C$_3$)alkanoyl;

i) X is absent, —P(=O)(OW)(O—), or —P(=O)(OW)—O—P(=O)(OW)(O—); and

Y is W, or

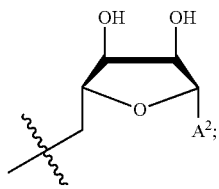

or ii) X is absent and Y is (C$_1$-C$_{10}$)alkanoyl;

R$^a$ is (C$_1$-C$_{10}$)alkyl, (C$_2$-C$_{10}$)alkenyl, or aryl, wherein each (C$_1$-C$_{10}$)alkyl, (C$_2$-C$_{10}$)alkenyl and aryl is optionally substitutes with one or more groups independently selected from the group consisting of halo, hydroxyl, cyano, (C$_1$-C$_3$)alkoxy, (C$_1$-C$_3$)alkoxycarbonyl, aryl, and (C$_1$-C$_3$)alkanoyloxy;

each W is independently selected from the group consisting of H and pharmaceutically acceptable cations;

A$^2$ is

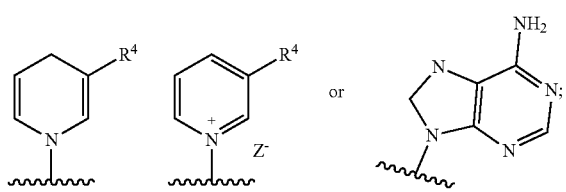

Z is a pharmaceutically acceptable anion;

R$^4$ is —COOH, —C(=O)NH$_2$ or —C(=O)OR$^b$; and

R$^b$ is (C$_1$-C$_{10}$)alkyl, (C$_2$-C$_{10}$)alkenyl, or aryl, wherein each (C$_1$-C$_{10}$)alkyl, (C$_2$-C$_{10}$)alkenyl and aryl is optionally substitutes with one or more groups independently selected from the group consisting of halo, hydroxyl, cyano, (C$_1$-C$_3$)alkoxy, (C$_1$-C$_3$)alkoxycarbonyl, aryl, and (C$_1$-C$_3$)alkanoyloxy.

13. A method comprising: promoting mammary gland development in a human female in need thereof, by administering to the human female, a compound of formula (I):

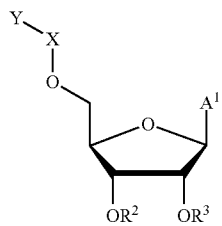

or a pharmaceutically acceptable salt thereof, wherein:
A$^1$ is

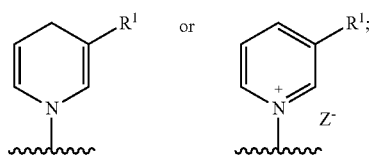

R$^1$ is —COOH, —C(=O)NH$_2$ or —C(=O)OR$^a$;
R$^2$ is H or (C$_1$-C$_3$)alkanoyl;
R$^3$ is H or (C$_1$-C$_3$)alkanoyl;
i) X is absent, —P(=O)(OW)(O—), or —P(=O)(OW)—O—P(=O)(OW)(O—); and
Y is W, or

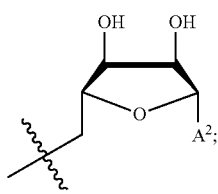

or
ii) X is absent and Y is (C$_1$-C$_{10}$)alkanoyl;
R$^a$ is (C$_1$-C$_{10}$)alkyl, (C$_2$-C$_{10}$)alkenyl, or aryl, wherein each (C$_1$-C$_{10}$)alkyl, (C$_2$-C$_{10}$)alkenyl and aryl is optionally substitutes with one or more groups independently selected from the group consisting of halo, hydroxyl, cyano, (C$_1$-C$_3$)alkoxy, (C$_1$-C$_3$)alkoxycarbonyl, aryl, and (C$_1$-C$_3$)alkanoyloxy;
each W is independently selected from the group consisting of H and pharmaceutically acceptable cations;
A$^2$ is

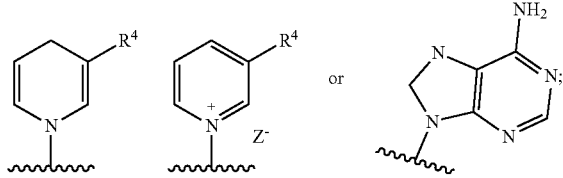

Z is a pharmaceutically acceptable anion;
R$^4$ is —COOH, —C(=O)NH$_2$ or —C(=O)OR$^b$; and
R$^b$ is (C$_1$-C$_{10}$)alkyl, (C$_2$-C$_{10}$)alkenyl, or aryl, wherein each (C$_1$-C$_{10}$)alkyl, (C$_2$-C$_{10}$)alkenyl and aryl is optionally substitutes with one or more groups independently selected from the group consisting of halo, hydroxyl, cyano, (C$_1$-C$_3$)alkoxy, (C$_1$-C$_3$)alkoxycarbonyl, aryl, and (C$_1$-C$_3$)alkanoyloxy.

14. A method comprising:
a) administering to a female mammal, a compound of formula (I):

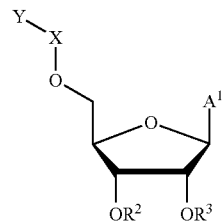

or a pharmaceutically acceptable salt thereof, wherein:
A$^1$ is

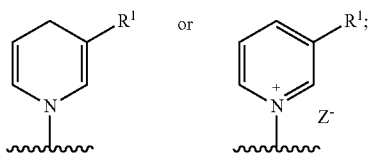

R$^1$ is —COOH, —C(=O)NH$_2$ or —C(=O)OR$^a$;
R$^2$ is H or (C$_1$-C$_3$)alkanoyl;
R$^3$ is H or (C$_1$-C$_3$)alkanoyl;
i) X is absent, —P(=O)(OW)(O—), or —P(=O)(OW)—O—P(=O)(OW)(O—); and
Y is W, or

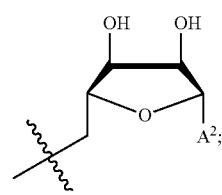

or
ii) X is absent; and Y is (C$_1$-C$_{10}$)alkanoyl;
R$^a$ is (C$_1$-C$_{10}$)alkyl, (C$_2$-C$_{10}$)alkenyl, or aryl, wherein each (C$_1$-C$_{10}$)alkyl, (C$_2$-C$_{10}$)alkenyl and aryl is optionally substitutes with one or more groups independently selected from the group consisting of halo, hydroxyl, cyano, (C$_1$-C$_3$)alkoxy, (C$_1$-C$_3$)alkoxycarbonyl, aryl, and (C$_1$-C$_3$)alkanoyloxy;
each W is independently selected from the group consisting of H and pharmaceutically acceptable cations;
A$^2$ is

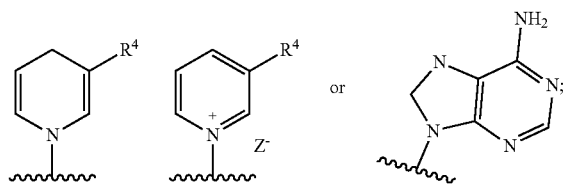

Z is a pharmaceutically acceptable anion;
R$^4$ is —COOH, —C(=O)NH$_2$ or —C(=O)OR$^b$; and
R$^b$ is (C$_1$-C$_{10}$)alkyl, (C$_2$-C$_{10}$)alkenyl, or aryl, wherein each (C$_1$-C$_{10}$)alkyl, (C$_2$-C$_{10}$)alkenyl and aryl is optionally substitutes with one or more groups independently selected from the group consisting of halo, hydroxyl, cyano, $(C_1-C_3)$alkoxy, $(C_1-C_3)$alkoxycarbonyl, aryl, and $(C_1-C_3)$alkanoyloxy; and b) measuring: (i) an increase in the firmness or size of a breast; (ii) an improvement in the shape of a breast; (iii) an increase in mammary gland mass or volume; or (iv) an increase in mammary gland development in the female mammal.

\* \* \* \* \*